United States Patent [19]
El-Sherbeini et al.

[11] Patent Number: 5,484,724
[45] Date of Patent: Jan. 16, 1996

[54] DNA ENCODING GLSI

[75] Inventors: Mohamed El-Sherbeini, Westfield; Joseph A. Clemas, Metuchen, both of N.J.

[73] Assignee: Merck & Co., Inc., Rahway, N.J.

[21] Appl. No.: 249,420

[22] Filed: May 26, 1994

[51] Int. Cl.$^6$ .............................. C12N 9/10; C12N 9/96; C12N 1/14; C12P 21/06

[52] U.S. Cl. .................. 435/193; 435/188; 435/189; 435/69.1; 435/252.3; 435/254.1; 435/254.2; 435/255.2; 536/22.1; 536/23.1; 536/23.7; 536/23.74

[58] Field of Search ..................................... 435/188, 189, 435/193, 69.1, 252.3, 254.1, 254.2, 255.2; 536/22.1, 23.1, 23.2, 23.7, 23.74

[56] References Cited

PUBLICATIONS

Breuder, Tamara et al., "Calcineurin is essential in cyclosporin A– and FK506–sensitive yeast strain", Proc. Natl. Acad. Sci. USA, vol. 91, pp. 5372–5376, Jun. 1994.
Koonin, Eugene et al., "Yeast chromosome III: New Gene Functions", The EMBO Journal, vol. 13, No. 3, pp. 493–503, 1994.

*Primary Examiner*—Robert A. Wax
*Assistant Examiner*—Hyosuk Kim
*Attorney, Agent, or Firm*—Christine E. Carty; Jack L. Tribble; Paul D. Matukaitis

[57] ABSTRACT

The DNA encoding glucan synthesis gene 1 (GLS1) is cloned and used in an in vitro assay to screen for compounds that modulate 1,3β-D glucan synthase activity.

6 Claims, 15 Drawing Sheets

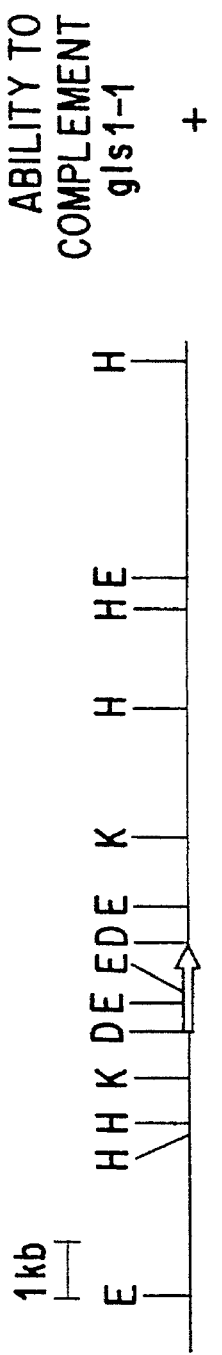
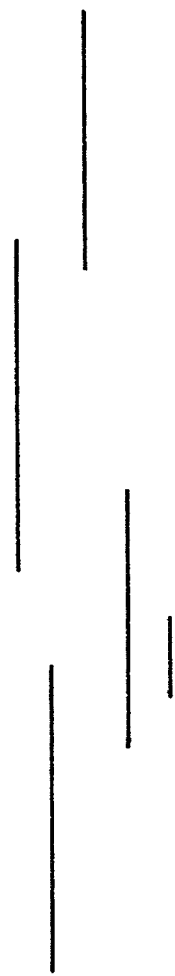
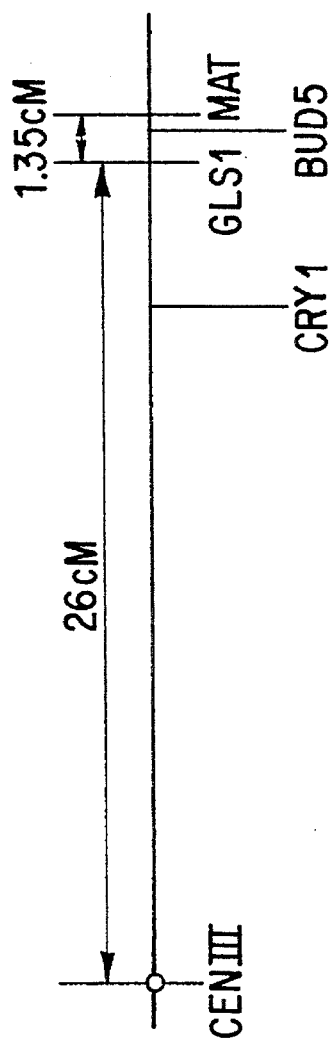
FIG. 6A
FIG. 6B
FIG. 6C

```
-600
       ATTTCAGCATGCTATTTCTCAAGGCACTCCTACTTTCCCTTTACCGGCCCCTCGCACTAGT
          -580                    -560
       CCAATAAGTCGTGCGCCTCCAAAGTTCAATTTTTCGAATGATCCGTTGGCAGCTTTGGCTG
          -540                    -520                    -500
       CGGTTGCCTCCGGCCAGATGCAATGAGCAGTTTTTTATCTAAAAGGAAATAATAATTG
          -480                    -460                    -440
       AACAAACGGCTGAGACGGGCAATACATTGCTCTACTTCTTTTTCCATCCAATGGTTGGTG
          -420                    -400                    -380
       AAACTCTCGAGCATACATTACCTTACGTGTTAGTGTACTATATTATATATATATATATAT
          -360                    -340                    -320
       GTATATATATATAAAGGGAGGAGTTTTAATTATAATTGTAATTTCGTATTTTTTCTGCATT
          -300                    -280                    -260
       ATACAGTTTTTTCCGATTTTAAACGACTTTATTTAAGTGTCGTTAAATATGTCACATTT
          -240                    -220                    -200
       TATTTTGTACGTATTCACATGTCCCTGGCCGTGCGCCATTGCTGAAAATCGCAAAACCCA
          -180                    -160                    -140
       CAGAGAAATAAACATGCGAAAAGTCAATGAAAATTGGAAAATATTTTTCATTTCACT
          -120                    -100                    -80
       ATTATCCACAAGCAATTTGTACAAGTGAACTAATTATCTTCGTCTAGAA
          -60                    -40                    -20
       GCCATGAATTCACTCGTTACTCAATATGCTGCTCCGTTGTTCGAGCGTTATCCCCAACTT
           1                    20                     40
           M  N  S  L  V  T  Q  Y  A  A  P  L  F  E  R  Y  P  Q  L
       CATGACTATTACCAACTTTGGAGCGACCATTTTTAATATTTCGTTGTGGGAACATTTC
           60                    80                    100
           H  D  Y  L  P  T  L  E  R  P  F  F  N  I  S  L  W  E  H  F
       GATGATGTCGTCACTCGTGTAACGGTAGATTTGTTCCAAGCGAATTCCAATTCATT
           120                    140                    160
           D  D  V  V  T  R  V  T  N  G  R  F  V  P  S  E  F  Q  F  I
```

```
                         200                           220
     GCAGGTGAATTACCATTAAGCACTTTGCCCCCTGTGCTATACGCCATCACTGCCTATTAC
 180 A  G  E  L  P  L  S  T  L  P  P  V  L  Y  A  I  T  A  Y  Y
                                 240                          260
     GTTATTATTTTTGGTGGCAGTTTTTGTTAAGTAAGTCGAAACCATTAAATTAAATGGC
     V  I  F  G  G  R  F  L  S  K  S  K  P  F  K  L  N  G
     300                          320                          340
     CTTTCCAATTGCATAATTTGGTTTTAACTTCACTTCATTGACGCTTTATTGCTTATG
     L  F  Q  L  H  N  L  V  L  T  S  L  S  L  T  L  L  L  L  M
                                 360                         380
     GTTGAACAATTAGTGCCAATTATTGTTCAGCACGGGTTATACTTCGCTATCTGTAATATT
     V  E  Q  L  V  P  I  I  V  Q  H  G  L  Y  F  A  I  C  N  I
     420                         440                          460
     GGTGCTTGGACTCAACCGCTCGTTACATTATATTACATGAATTACATTGTCAAGTTTATT
     G  A  W  T  Q  P  L  V  T  L  Y  Y  M  N  Y  I  V  K  F  I
                                 480                          500
     GAATTTATAGACACCTTTTTTCTTGGTGCTAAAACATAAAAAATTGACATTTTGCATACT
     E  F  I  D  T  F  F  L  V  L  K  H  K  K  L  T  F  L  H  T
     540                         560                          580
     TATCACCATGGCGCTACTGCCTATTATGTTACACCCAATTGATGGGCACCACATCTATT
     Y  H  H  G  A  T  A  L  L  C  Y  T  Q  L  M  G  T  T  S  I
                                 600                          620
     TCTTGGGTCCCTATTTCATTGAACCTTGGTGTTCACGTGTTATGGTATTGGTACTATTTC
     S  W  V  P  I  S  L  N  L  G  V  H  V  V  M  Y  W  Y  Y  F
     660                         680                          700
     TTGGCTGCCAGAGGCATCAGGGTCTGGTGGAAGGAATGGGTTACCAGATTTCAAATTATC
     L  A  A  R  G  I  R  V  W  W  K  E  W  V  T  R  F  Q  I  I
```

FIG. 9C

```
      720                          740                           760
CAATTTGTTTTGGATATCGGTTTCATATATTTTGCTGTCTACCAAAAAGCAGTTCACTTG
 Q  F  V  L  D  I  G  F  I  Y  F  A  V  Y  Q  K  A  V  H  L
             780                          800                          820
TATTTCCAATTTGCCACATTGTGGTGACTGTGGGGTTCAACTGCCACCTTTGCA
 Y  F  P  I  L  P  H  C  G  D  C  V  G  S  T  A  T  F  A
       840                          860                          880
GGTTGTGCCATTATTCTTCATATTTGGTACTATTATTTCATTTTACATTAACGTTTAT
 G  C  A  I  I  S  S  Y  L  V  L  F  I  S  F  Y  I  N  V  Y
             900                          920                          940
AAACGTAAAGGCACCAAAACCAGTAGAGTGGTAAAGCGTGCCCACGGCGGTGTTGCCGCA
 K  R  K  G  T  K  T  S  R  V  V  K  R  A  H  G  G  V  A  A
       960                          980                          1000
AAGGTTAATGAGTATGTTAACGTTGACTTGAAAAACGTTCCTACTCCATCCACCA
 K  V  N  E  Y  V  N  V  D  L  K  N  V  P  T  P  S  P  S  P
             1020                         1040                         1060
AAACCTCAACACAGAAGAAAAAGGTAAGTGTAAAAATCTTTGAAAGAATTTAAGTATTCAA
 K  P  Q  H  R  R  K  R
       1080                         1100                         1120
CTTTCGTATATTCGTTTTTTCTTAGTGGATCTATTGTTACTATTATCACTATTATTATAT
             1140                         1160                         1180
TGTAAAAGACCGGATGGTTTGTTTATATATTACATACACATGTTATCGTTGAAAAAAGTT
       1200                         1220                         1240
TTCCGTTTCCTTTCGACAGTCATCAGATAAATTTTATCCGAGTCTTTTATAT
```

DNA ENCODING GLSI

BACKGROUND OF THE INVENTION

A DNA molecule containing a gene which reverses a mutant phenotype of a strain of *Saccharomyces cerevisiae* is isolated and purified. The gene is GLS1 (glucan synthesis gene 1). GLS1 encodes a subunit of 1,3-β-D glucan synthase. The protein encoded by GLS1 represents a target for drug therapy for fungal disease. The invention includes homologues of GLS1 is isolated from other fungi, such as *Aspergillus fumigatus*, *Candida albicans*, *Schizosaccharomyces pombe* and *Phytophthora infestans*.

Understanding the mode of action of therapeutic compounds requires a variety of experimental approaches. One approach involves the isolation of organisms resistant or sensitive to test compounds. Such organisms may be used to isolate genes encoding the drag targets.

The fungal cell wall is a complex structure composed of a number of polymers: chitin, α- and β-glucans, and mannoproteins. The fungal cell wall is involved in a variety of vital cellular processes: vegetative growth, morphogenesis, uptake and secretion of macromolecules and protection against osmotic changes are affected by changes in the composition and integrity of the cell wall. Antifungal compounds which act via the inhibition of cell wall synthesis (a process essential to fungi and absent from mammalian cells) may have high fungicidal activity and low toxicity to mammalian cells.

One class of β-glucan inhibitors is comprised of lipopeptide antibiotics such as aculeacin A, echinocandin B and the pneumocandins. These compounds are cyclic hexapeptides that contain a non-polar fatty acid side chain. Echinocandins are fungicidal because they inhibit synthesis of 1,3-β-D glucan, which disrupts the integrity of the cell wall and causes lysis of yeast cells. In vitro echinocandins inhibit polymerization of glucose into 1,3-β-D glucan.

Another class of β-glucan synthesis inhibitors comprises the papulacandins and chaetiacandin. These compounds contain a glycoside component connected to an aromatic ring system and two long chain fatty acids. These compounds have the same mode of action as the echinocandins.

It has been shown that *Pneumocystis carinii* has β-glucan in the wall of its cyst form (Matsumoto, Y., et al., 1989, *J. Protozool.* 36:21S-22S). Inhibitors of β-glucan synthesis, such as papulacandins and echinocandins, may be useful in the treatment of *P. carinii* infections. In a rat model of *P. carinii* pneumonia, L-67 1,329 (an echinocandin) and L-687,781 (a papulacandin) were both effective in reducing the number of cysts in the lungs of infected rats (D. M. Schmatz et al., 1990, *PNAS* 87:5950–5954). These results suggest that β-glucan synthesis is a target for the identification of therapeutics useful in the treatment of *P. carinii* infections.

There have been a number of efforts to isolate drug-resistant yeast strains affected in β-glucan synthesis. The mutants that have been isolated include acul (Mason, M. M., et al. 1989, Cold Spring Harbor Laboratory, Abstract # 154), and papl (Duran, A., et al., 1992, *Profiles in Biotechnology* (T. G. Villa and J. Abalde, Eds.) Serivicio de Publicaciones, Universidad de Santiago, Spain. pp. 221–232).

In the present work a more potent echinnocandin (L-733,560) was used as a selective agent to isolate mutant strains specifically affected in glucan synthesis. One mutant (strain MS14) is echinocandin-resistant and is also supersensitive to the chitin synthase inhibitor nikkomycin Z. The mutation in MS14 maps to the FKS1 gene and is designated fks1-4. Another mutant (strain MS1) is resistant to echinocandins and supersensitive to both papulacandin and rapamycin. Strain MS1 was used to clone the GLS1 gene.

SUMMARY OF THE INVENTION

A DNA molecule encoding a protein involved in biosynthesis of 1,3-β-D glucan (GLS1) is identified, cloned, expressed and used in assays to screen for antifungal compounds.

BRIEF DESCRIPTION OF THE DRAWINGS

FIG. 6. Localization of the gls1-1 minimum complementing fragment. A partial restriction map of the 17-kb clone containing gls1-1 complementing activity is depicted (A). The direction of transcription of GLS1 is indicated by the arrow. The yeast genomic DNA fragments represented by the lines below the restriction map (B) were inserted into the centromefic plasmid YCP50. The recombinant plasmids were transformed into MS1 (gls1-1 mutant). Transformed cells were tested for complementation of the echinocandin-resistance phenotype. The plasmids as represented from the top to the bottom are pJAC2, pHF, pEF. Abbreviations for restriction enzymes: D, DpnI; E, EcoRI; H, HindIII; K, KpnI.

FIG. 9. Nucleotide and predicted amino acid sequences of the *S. cerevisiae* GLS1.

DETAILED DESCRIPTION OF THE INVENTION

Figure 1A:
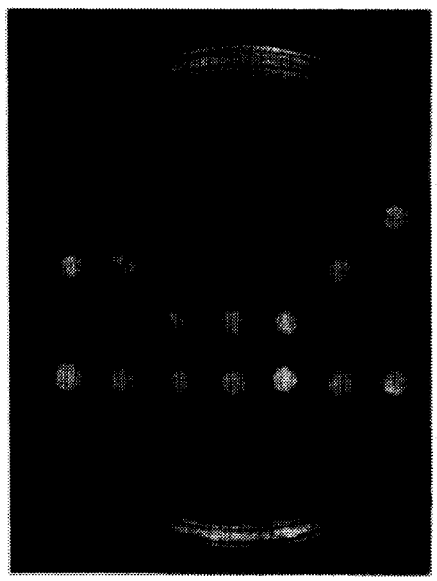
FIG. 1. Segregation pattern (2:2) of meiotic products indicating single gene mutations conferring resistant to echinocandins. Cells representing the 4 meiotic products of tetrads resulting from a crosses between MS1 and the wild-type strain GG100-14D were spotted on media containing 7.5 μM of L,733-560. Following growth at 28° C. for two days, two of four segregants were able to grow indicating the 2:2 segregation of the drug-resistance phenotype.
Figure 1B:
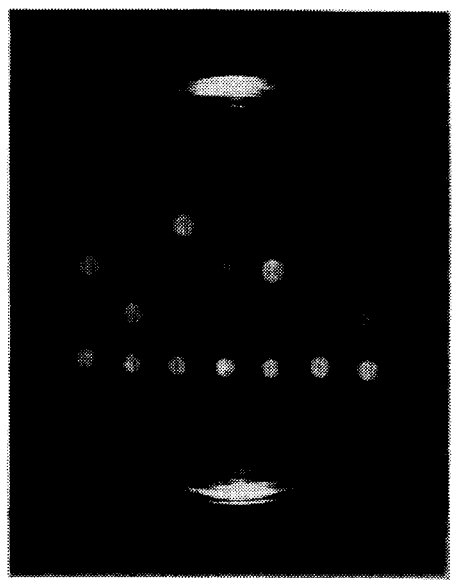
Figure 1C:
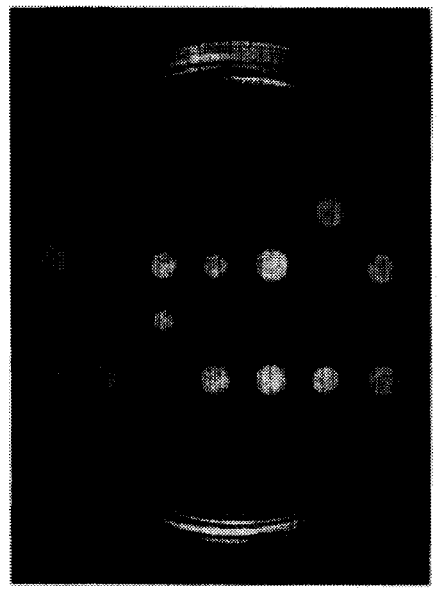
Figure 1D:
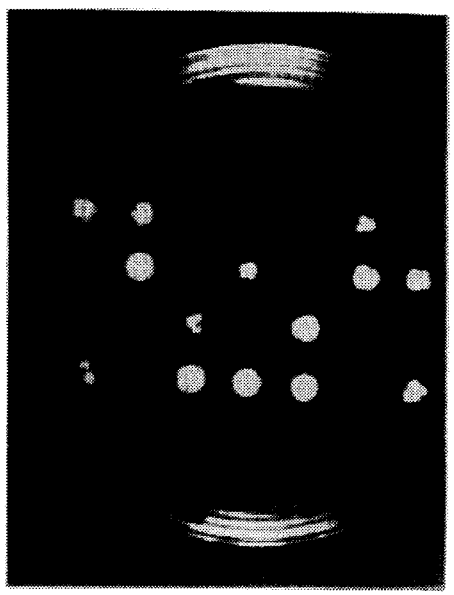

A DNA molecule encoding a protein involved in biosynthesis of 1,3-β-D glucan (GLS1) is identified, cloned, expressed and used in assays to screen for antifungal compounds.

Antifungal compounds are used for treatment of fungal infections in animals, including humans. There is increasing demand for safer and more effective antifungal compounds. Because the structure of the fungal cell wall differs from the structure of mammalian cell membranes, compounds that specifically interfere with the maintenance or biosynthesis of the fungal cell wall are targets of drug screens.

Cell wall biosynthesis is fundamental to the maintenance and growth of fungi and plants. Cell walls provide skeletal support and mechanical protection of the protoplasts from the environment. Functions such as the selective uptake of macromolecules, osmoregulation, cell growth and cell division occur in the cell wall. Enzymatic activities related to hydrolysis of extracellular nutrients and turnover of the cell wall macromolecules during morphogenesis are associated with the extracellular matrix.

Polysacchafides account for as much as 80–90% of the cell wall of *S. cerevisiae*. The major cell wall polymers are glucan and mannan; in addition, small amounts of chitin are present(Cabib, E. 1991, *Antimicrob. Agents Chemother.* 35:170–173). It is believed that glucan supports and maintains rigidity of the cell wall while mannoproteins regulate its permeability (Zlotnik et all., 1984).

Three types of glucan account for 30–60% of the cell wall of *S. cerevisiae* (Fleet, G. H., 1985, p. 24–56. In M. R. McGinnis (ed.), *Current Topics in Medical Mycology* Vol. I. Springer, Verlag, N. Y.). The major form of glucan (60% of the total) is insoluble in alkali or acetic acid, is a branched 1-3-βpolymer, has fibrillar structures containing 3% of 1-6-βinterchain linkages, and lacks 1-6-β interresidue linkages. A second form of glucan (32% of the total) is soluble in dilute alkali, has an amorphous structure and contains mainly 1-3-βlinkages with some 1-6-βlinkages. A minor form of glucan (8% of the total) is acid-soluble, highly-branched and contains mainly 1-6-β linkages.

Echinocandins interfere with cell wall biosynthesis, most likely by inhibiting the synthesis of 1,3-β-glucan. A key enzyme in the cell wall formation is the 1,3-βglucan synthase. This enzyme is absent from animal cells, making it a target for development of antifungal compounds. 1,3-βglucan synthase is a membrane-associated enzyme that uses UDP-glucose as a substrate and is stimulated by a detergent-soluble GTP-binding protein (Kang, M. S. and E. Cabib. *Proc, Natl. Acad. Sci. USA* 83:5808–5812).

The techniques used to isolate drug-resistant mutants are similar to those used to isololate auxotrophic, temperature-sensitive, and UV-sensitive mutants, such as described (Sherman et al., 1986).

The GLS1 gene may be isolated from a chromosomal DNA library by complementation of a mutation (gls1-1) which renders cells resistant to echinocandins (Sherman et al., 1986). The GLS1 gene may be isolated from chromosomal DNA by preparing a library of DNA fragments in a DNA cloning vector and screening individual clones for the presence of GLS1. For example, a library of *S. cerevisiae* genomic DNA from strain GRF88 in the plasmid YCp50 can be obtained from the American Type Culture Collection, 12301 Parklawn Drive, Rockville, Md. 20852, as ATCC 37415.

A plasmid library may be prepared by isolating chromosomal DNA from pure cultures of the microorganisms. The chromosomal DNA is fragmented for example, by partial digestion with one or more restriction endonuclease enzymes. The resulting DNA fragments are separated by size and may then fragments are inserted into a cloning vector.

The cloning vector is cut with at least one restriction endonuclease, treated with phosphatase, and the DNA fragments are ligated with a DNA ligase. The cloning vectors are used to transform host cells competent for the uptake of DNA. Host cells for cloning, DNA processing, and expression include but are not limited to bacteria, yeast, fungi, insect cells and mammalian cells. *Escherichia coil* K-12 strains RR1, HB101, JM109, DH11S, or DH5a are useful host cells. When about $5\times10^4$ independent genomic DNA fragments are ligated into a cloning vector, a library is formed. A complete library is likely to contain a representation of the entire genome. Competent host cells which take up and stably maintain a recombinant DNA molecule in the transformation procedure can be identified by their ability to grow on medium supplemented with a plasmid-selective drug. For plasmid vectors containing the ampicillin resistance gene, ampicillin is the selective drug. To obtain full representation of a library, transformation mixtures are spread on agar plates and incubated under appropriate conditions. Transformed cells are resuspended from the surface of agar plates in a small volume of liquid medium. The cell suspension is used to inoculate a larger volume of liquid medium supplemented with the selective drug, and incubated overnight at 37° C. Plasmid DNA is then extracted from the cells by methods known in the art.

Screens to identify the GLSI gene in the plasmid library can be devised. One strategy requires the use of a gls1-1 mutant of *S. cerevisiae*, such as strain D2-8B or strain D2-8D. Cells are made competent to take up DNA and then transformed with library DNA. Transformants bearing the GLS1 gene will exhibit a plasmid-dependent increase in sensitivity to a selective echinocandin.

Aliquots of the transformation mixture are plated on selective media. Colonies of transformants may be collected, resuspended in liquid medium, pooled, and stored frozen at −80° C. in medium supplemented with 25% glycerol. The titer, defined as the number of colony forming units per milliliter, is determined by methods known in the art.

Identification of transformants that contain the GLS1 gene is accomplished by plating the library onto agar plates containing plasmid-selective medium such that a countable number of colonies grow on each plate. A portion of each colony is transferred to two agar plates by replica plating: one plate contains plasmid-selective medium supplemented with a concentration of the selective echinocandin which kills the cells with intermediate sensitivity, and a second plate contains plasmid-selective medium only. Positive clones grow normally on the plate without echinocandin but grow poorly or not at all on the echinocandin-containing plate.

The echinocandin-sensitive phenotype of potential clones may be detected by a variety of tests. In one test, cells from a colony are patched directly onto the surface of plates containing different concentrations of the selective echinocandin. The test is scored after two days of incubation. Cells that grow poorly in the presence of the drug are potential positives and are likely to contain plasmids carrying the complementary gene.

In a second test, a portion of each colony is transferred by replica plating to an agar plate containing the selective echinocandin at a concentration approximately twice that used in the first test. Positive clones (clones that are sensitive to echinocandin) do not grow on these plates.

In a third test, cells from a colony are inoculated into plasmid-selective liquid medium and grown to saturation. An aliquot of the saturated culture is used to inoculate fresh liquid medium supplemented with or without the selective echinnocandin. Growth is measured by optical density at a wavelength of 600 nm. Colonies that do not grow in the presence of echinocandin are scored echinocandin-sensitive.

In another test, clones are tested in a broth microdilution assay, wherein a range of concentrations of the selective echinocandin are tested. Positive clones are more sensitive to the selective echinocandin than the original resistant mutant.

Tests such as those described above may be used to screen a library of genomic DNA so as to identify a recombinant plasmid that contains a functional copy of the GLS1 gene. To determine whether an increase in sensitivity to echmocandin is due to a plasmid-encoded copy of GLS1, positive clones are cured of plasmid DNA and tested for a decrease in sensitivity to echinocandin. If increased echinocandin sensitivity is due to the presence of the plasmid, then plasmid loss results in the loss of this phenotype.

More direct proof that an increase in sensitivity to echinocandin is due to the presence of a plasmid containing the GLS1 gene may be obtained by isolating plasmid DNA from a positive clone. Cells of *E. coli* competent to take up DNA are transformed with the plasmid, and transformants are identified and isolated. Plasmid DNA is isolated from the transformed *E. coli* and then digested with restriction endonucleases to yield fragments of discrete sizes. The size of each fragment is estimated by conventional methods, such as gel electrophoresis. By digesting the plasmid with a variety of enzymes, a cleavage map is generated. The cleavage map is distinct and specific for the cloned fragment. A detailed cleavage map is sufficient to identify a particular gene within the genome. Fragments of the cloned gene, generated by digestion with endonucleases, may be purified from agarose gels and ligated into vectors suitable for sequencing by methods known in the art. Vectors include, but are not limited to pUC18, pUC19, YEp24, pGEM3Zf(+), pGEM5Zf(+), and pGEM7Zf(−).

The GLS1 gene of *S. cerevisiae* may be used to isolate and characterize homologous genes in pathogenic fungi. Because other fungi, which include but are not limited to strains of *C. neoformans, C. albicans, A. fumigatus,* and *Phytophthora infestans* have 1,3-β-D glucan in their cell walls, it is likely that a functional homologue of GLS1 exists in each of these fungi. Functional homologues of GLS1 may exist in other organisms that have 1,3-β-D glucans in their cell walls.

GLS1 homologues may be detected by isolating chromosomal DNA from a test organism. A portion of the isolated chromosomal DNA is cut with a number of restriction enzymes. The digested fragments of DNA are separated by gel electrophoresis. The fragments are then transferred to a solid membrane support. The membrane is then hybridized overnight with a labeled probe. The blot is washed and then exposed to XAR-5 film and developed by conventional methods (Laskey and Mills (1977) FEBS Letters, 82: 314–316). The conditions for washing the blot are such that only DNA fragments with a high degree of homology (estimated at ≧80%) will hybridize to the probe. The size and pattern of the digested fragments which hybridize with the probe generate a genomic map. For each organism, the map is sufficient to specifically identify the GLS1 homologue in the chromosome.

Mutations of the GLS1 gene, including but not limited to glsl-1 (strain MS1), gls1-2 (strain MS41) and gls1-3 (strain MS43), or disruptions or deletions of GLS1, are useful for screening for glucan synthase inhibitors. Such a screen relies on the increase in echinocandin-resistance and in papulacandin sensitivity of such mutants compared to an GLS1 wild-type strain. Any technique capable of detecting this difference in sensitivity can be used. A zone of inhibition assay on agar plates is particularly useful.

Cloned GLS1 cDNA may be recombinantly expressed by molecular cloning into an expression vector containing a suitable promoter and other appropriate transcription regulatory elements, and transferred into prokaryotic or eukaryotic host cells to produce recombinant GLS1.

Expression vectors are defined herein as DNA sequences that are required for the transcription of cloned copies of genes and the translation of their mRNAs in an appropriate host. Such vectors can be used to express eukaryotic genes in a variety of hosts such as bacteria, yeast, bluegreen algae, plant cells, insect cells and animal cells.

Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant GLS1 in mammalian cells. Commercially-available mammalian expression vectors which may be suitable for recombinant GLS1 expression, include but are not limited to, pMCl neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

DNA encoding GLS1 may also be cloned into an expression vector for expression in a recombinant host cell. Recombinant host cells may be prokaryotic or eukaryotic, including but not limited to bacteria, yeast, mammalian cells and insect cells. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, infection, protoplast fusion, and electroporation. The expression vector-containing cells are clonally propagated and individually analyzed to determine whether they produce GLS1 protein. Identification of GLS1 expressing host cell clones may be done by several means, including but not limited to immunological reactivity with anti-GLS1 antibodies, and the presence of host cell-associated GLS1 activity.

Expression of GLS1 cDNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

To determine the GLS1 cDNA sequence(s) that yields optimal levels of enzymatic activity and/or GLS1 protein, modifed GLS1 cDNA molecules are constructed. Host cells are transformed with the cDNA molecules and the levels of GLS1 RNA and protein are measured.

Levels of GLS1 protein in host cells are quantitated by a variety of methods such as immunoaffinity and/or ligand affinity techniques. GLS1-specific affinity beads or GLS1-specific antibodies are used to isolate $^{35}$S-methionine labelled or unlabelled GLS1 protein. Labelled GLS1 protein is analyzed by SDS-PAGE. Unlabelled GLS1 protein is detected by Western blotting, ELISA or RIA assays employing GLS1 specific antibodies.

Following expression of GLS1 in a recombinant host cell, GLS1 protein may be recovered to provide GLS1 in active form. Several GLS1 purification procedures are available and suitable for use. Recombinant GLS1 may be purified from cell lysates or from conditioned culture media, by various combinations of, or individual application of fractionation, or chromatography steps that are known in the art.

In addition, recombinant GLS1 can be separated from other cellular proteins by use of an immuno-affinity column made with monoclonal or polyclonal antibodies specific for full-length nascent GLS1 or polypeptide fragments of GLS1.

The recombinant protein may be used to generate antibodies. The term "antibody" as used herein includes both polyclonal and monoclonal antibodies, as well as fragments thereof, such as, Fv, Fab and F(ab)2 fragments that are capable of binding antigen or hapten.

Monospecific antibodies to GLS1 are purified from mammalian antisera containing antibodies reactive against GLS1 or are prepared as monoclonal antibodies reactive with GLS1 using standard techniques. Monospecific antibody as used herein is defined as a single antibody species or multiple antibody species with homogenous binding characteristics for GLS1. Homogenous binding as used herein refers to the ability of the antibody species to bind to a specific antigen or epitope, such as those associated with the GLS1, as described above. Enzyme-specific antibodies are raised by immunizing animals such as mice, rats, guinea pigs, rabbits, goats, horses and the like, with rabbits being preferred, with an appropriate concentration of GLS1 either with or without an immune adjuvant.

Monoclonal antibodies (mAb) reactive with GLS1 may be prepared by conventional methods, such as by immunizing inbred mice with GLS1.

In vitro production of anti-GLS1 is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of GLS1 in body fluids or tissue and cell extracts.

Methods such as those described above may be used to produce monospecific antibodies may be utilized to produce antibodies specific for GLS1 polypeptide fragments or full-length nascent GLS1 polypeptide.

Kits containing GLS1 cDNA, antibodies to GLS1 or GLS1 protein may be prepared. Such kits are used to detect DNA which hybridizes to GLS1 DNA or to detect the presence of GLS1 protein or peptide fragments in a sample. Such characterization is useful for a variety of purposes including but not limited to forensic analyses, taxonomic determinations and epidemiological studies.

The DNA molecules, RNA molecules, recombinant protein and antibodies of the present invention may be used to screen and measure levels of GLS1 DNA, GLS1 RNA or GLS1 protein. The recombinant proteins, DNA molecules, RNA molecules and antibodies lend themselves to the formulation of kits suitable for the detection and typing of GLS1. Such a kit would comprise a compartmentalized carder suitable to hold in close confinement at least one container. The carder would further comprise reagents such as recombinant GLS1 protein or anti-GLS1 antibodies suitable for detecting GLS1. The carder may also contain means for detection such as labeled antigen or enzyme substrates or the like.

Because the genetic code is degenerate, more than one codon may be used to encode a particular amino acid, and therefore, the amino acid sequence can be encoded by any of a set of similar DNA oligonucleotides. Only one member of the set will be identical to the GLS1 sequence but will be capable of hybridizing to GLS1 DNA even in the presence of DNA oligonucleotides with mismatches. The mismatched DNA oligonucleotides may still hybridize to the GLS1 DNA to permit identification and isolation of GLS1 encoding DNA.

DNA encoding GLS1 from a particular organism may be used to isolate and purify homologues of GLS1 from other organisms. To accomplish this, the first GLS1 DNA may be mixed with a sample containing DNA encoding homologues of GLS1 under appropriate hybridization conditions. The hybridized DNA complex may be isolated and the DNA encoding the homologous DNA may be purified therefrom.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate.

As used herein, a "functional derivative" of GLS1 is a compound that possesses a biological activity (either functional or structural) that is substantially similar to the biological activity of GLS1. The term "functional derivatives" is intended to include the "fragments," "variants," "degenerate variants," "analogs" and "homologs" or to "chemical derivatives" of GLS1. The term "fragment" is meant to refer to any polypeptide subset of GLS1. The term "variant" is meant to refer to a molecule substantially similar in structure and function to either the entire GLS1 molecule or to a fragment thereof. A molecule is "substantially similar" to GLS1 if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire GLS1 molecule or to a fragment thereof.

The present invention is also directed to methods for screening for compounds which modulate that expression of DNA or RNA encoding GLS1 as well as the function of GLS1 protein in vivo. Compounds which modulate these activities may be DNA, RNA, peptides, proteins, or non-proteinaceous organic molecules. Compounds may modulate by increasing or attenuating the expression of DNA or RNA encoding GLS1 or the function of GLS1 protein. Compounds that modulate the expression of DNA or RNA encoding GLS1 or the function of GLS1 protein may be detected by a variety of assays. The assay may be a simple "yes/no" assay to determine whether there is a change in expression or function. The assay may be made quantitative by comparing the expression or function of a test sample with the levels of expression or function in a standard sample.

The following examples are provided to further define the invention without, however, limiting the invention to the particulars of these examples.

EXAMPLE 1

Strains, Plasmids and Media

The yeast strains used in this study are listed in Table 1. The mutant strains are derived from strain X2180-1A.

TABLE 1

| Strain | Relevant Properties |
|---|---|
| X2180-1A | MATa GLS1 (wt, Ech$^S$) |
| MS1 | MATa gls1-1 (Ech$^R$) |
| MS41 | MATa gls1-2 (Ech$^R$) |
| MS7-43 | MATa gls1-3 (Ech$^R$) |
| GG100-14D | MATα GLS1 (wt, Ech$^S$) |
| D2 | MATa/MATα (MS41 × GG 100-14D) |
| D12 | MATa/MATα (MS1 × GG100-14D) |
| D28 | MATa/MATα (MS7-43 × GG100-14D) |
| D132 | MATa/MATα (D28-18C × D28-3B) |
| D136 | MATa/MATα (D28-18C × D2-1D) |
| D137 | MATa/MATα (D28-18C × D12-11D) |
| D140 | MATa/MATα (D28-9D × D2-1B) |
| D141 | MATa/MATα (D12-7D × D2-1B) |
| D142 | MATa/MATα (D2-2D × D2-1B) |
| D2-1B | MATα ura3-52 gls1-2 |

TABLE 1-continued

| Strain | Relevant Properties |
|---|---|
| D2-1D | MATa ura3-52 gls1-2 |
| D2-2D | MATa his3 gls1-2 |
| D12-7D | MATa his3 gls1-1 |
| D12-11D | MATa ura3-52 gls1-3 |
| D28-3B | MATa his3 gls1-3 |
| D28-9D | MATa his3 gls1-3 |
| D28-18C | MATa ura3-52 his3 gls1-3 |
| D2-5A | MATα his3 ura3-52 GLS1 |
| MS100 | MATα his3 trp1 gls1::URA3-52 |
| MS101 | MATα his3 gls1::URA3-52 |

Strains GG100-14D and X2180-1A were obtained from K. Bostian and C. Ballou respectively. The mutants were generated in X2180-1A and outcrossed to GG 100-14D. Abbreviations: wt, wild-type; Ech, echinnocandin; S, sensitive; R, resistance.

| Plasmid | Description | Source of cloned DNA |
|---|---|---|
| pJAC2 | 16-Kb GLS1 clone in YCp50 | GRF88 |
| pJAC1 | 4-kb GLS1 clone in YCp50 | GRF88 |
| pJAC4 | 4-Kb GLS1 clone in YEP24 | GRF88 |

The media used are as follows. YPAD medium contains 1% Bacto Yeast Extract, 2% Bacto-Peptone, 2%; Dextrose, 0.003%; and adenine sulfate. Synthetic Dextrose (SD) Medium contains 0.67% Bacto Yeast Nitrogen Base without amino acids (Difco), 2% Dextrose and 2% Bacto Agar (Difco). Synthetic Complete (SC) medium is SD medium supplemented with 20 mg each of adenine, histidine, and uracil, 60 mg of leucine, 30 mg of lysine, and 20 mg of tryptophan per liter of medium. Sporulation medium is 2% Bacto Agar (Difco) and 0.3% potassium acetate. Ura dropout medium is SC medium without uracil. Solid media are prepared with approximately 20 g/L agar.

EXAMPLE 2

DNA Manipulation and Transformation

Standard techniques of DNA manipulation were utilized (Sambrook, J., E. F. Fritsch, and T. Maniatis. 1989. *Molecular Cloning: a laboratory. manual,* 2nd ed. Cold Spring Harbor Laboratory Press, Cold Spring Harbor, N.Y.). *E. coli* strain DH5a (Hanahan, D. 1983. Studies on transformation of *Escherichia coli* with plasmids. *J. Mol. Biol.* 166:557–580) was used as the host in bacterial transformation. Yeast transformation with the DNA libraries was performed by electroporation (Becker, D. and L. Guarente. 1991. High-efficiency transformation of yeast by electroporation. In C. Guthrie and G. Fink (eds.), *Guide to yeast genetics and molecular biology. Methods Enzymol.* 194:182–187.). All other yeast transformations with different plasmid subclones were by the alkali cation method (Ito, H., M. Fukuda, M. Murata, and A. Kimura. 1983. Transformation of intact yeast cells with alkali cations. *J. Bacteriol.* 153:63–68). Plasmid DNA was prepared from *E. coli* by the alkaline lysis method (Sambrook, J., et al., supra). Plasmids were isolated from yeast for transformation into *E. coli* as previously described (Hoffman, C. S. and F. Winston. 1987. A ten-minute DNA preparation from yeast efficiently releases autonomous plasmids for transformation of *Escherichia coli*. *Gene* 57: 267–272). The wild-type gene, GLS1, which complements the echinocandin-resistance phenotype of the MS1 strain was isolated from a yeast genomic DNA library constructed in the centromeric shuttle vector YCp50 (Rose, M.D., P. Novick, J. H. Thomas, D. Botstein, and G. R. Fink. 1987. *Gene.* 60:237–243) as described below.

EXAMPLE 3

The nucleotide sequences of the GLS1 5' and the 3' ends were determined by the dideoxy chain termination method (Sanger, F. S. Nicklen, and A. Coulson. 1977. "DNA sequencing with chain-terminating inhibitors". *Proc. Natl. Acad. Sci. USA* 74:5463–5467, 1977), using synthetic oligonucleotide primers complementary to specific regions of GLS1 and a sequenase reagent kit (U.S. Biochemical Corp.).

EXAMPLE 4

PCR Amplification

The polymerase chain reactions (PCR) were performed according to published procedures (Mullis, K. B. and F. A. Faloona, 1987. Specific synthesis of DNA in vitro via a polymerase-catalyzed chain reaction. *Meth. Enzymol.* 155:335–350). Approximately 5 ng of genomic DNA from strain X2180-1A was used as a template. Synthetic oligonucleotide primers were designed to amplify a 1.5-kb fragment of a region 5-kb to the left of the MAT locus on chromosome III. The sequence of the two primers were:
5'-TGACAGTAGTYFCACAAGTACT-
   TAATATIGGAAATG-3'(SEQ ID NO.:1) and
5'-TCAGATAATTTTATCGGTACCTTTTATATGTTAAAT-
   3'(SEQ ID NO.:2).

Amplified DNA fragments were gel-purified, radiolabelled by the random priming method (Feinberg, A. P and B. Vogelstein. 1984. *Anal. Biochem.* 137:266) and used as probes to screen bacterial colonies containing a yeast genomic DNA library in the centromeric vector YCp50 (Rose, M.D., et al., supra) following published protocols (Sambrook, J., et al., supra).

EXAMPLE 5

Gene Disruption

Chromosomal disruption of the GLS1 gene was performed by one-step gene disruption protocol (Rothstein, R. J. 1983. *One-step gene disruption in yeast. Methods Enzymol.* 101:202–211). Plasmid pJAC4 was constructed by cloning of a 1.6-kbp DpnI fragment from pJAC2-1 into the HincII site of pUC18. Double digestion of pJAC4 with NruI-EcoRV resulted in the excision of a 1.2-kb fragment containing all but the 40 C-terminal amino acids encoded by GLS1. A 1.5-kb DNA fragment carrying the *S. cerevisiae* URA3 gene was isolated from the YCp50 plasmid as a NruI-SmaI fragment. The purified fragment was treated with T4 DNA polymerase and blunt-end ligated into the NruI-EcoRV sites of GLS1 on plasmid pJAC4 resulting in plasmid pJAC9 which contains a disruption deletion of GLS1. Plasmid pJAC9 was propagated in *E. coli*, and the structure of the plasmid was verified by restriction analysis.

The glsl::URA3 disruption fragment was purified from pJAC9 as 2.7 kb XbaI-HindIII fragment that was used to transform ura 3-52 yeast strains containing a wild-type GLS1 gene (strains GG100-14D and D2-5A). Uracil prototrophic yeast transformants were selected on SC medium lacking uracil. From each of the two transformed strains, one Ura$^+$ transformant was purified by single colony formation. Three Ura$^+$ single colonies from each of the two transformants were tested for L-733,560-resistance and shown to exhibit drug resistance. These colonies were further characterized and the integration event at the GLS1 locus was confirmed by Southern hybridization (Sambrook, J., et al., supra). The two mutants resulting from disruption the GLS1 gene in GG100-14D and D2-5A were designated MS100 and MS101, respectively.

Total genomic DNA was isolated from stationary cultures of strains GG100-14D, D2-SA, MS100 and MS101. Approximately 5 μg amounts of each DNA were restriction digested with DraI. The digestion products were resolved on 1% agarose gels, followed by transfer to Zeta probe GT nylon membranes and hybridization according to the manufacturers protocols (Biorad Laboratories). A $^{32}$p radiolabeled probe of a DraI fragment, internal to GLS1, was prepared by the random primer method (Feinberg, A. P and B. Vogelstein. 1984. *Anal. Biochem.* 137:266).

EXAMPLE 6

Liquid Broth Microdilution Assay

To quantitate the echinocandin sensitivity/resistance of the mutant strains, yeast cells grown to log phase were inoculated into 2 ml SC broth and incubated overnight at 28° C. A flat bottom 96-well microtiter plate was seeded with 75 μl of SC medium in columns 2 through 12. To column 1, 150 μl medium was added. Echinocandin (L-733,560) was prepared at a concentration of 30 μg/ml solution in sterile distilled water. An aliquot (75 μl) of echinocandin solution was added to column 3, and 75 μl from column 3 was transferred to column 4, followed by mixing of the contents of each well. 75 μl from column 4 was transferred into column 5, and the serial dilution was carried on to column 12 from which a 75 μl was discarded. A dilution of 6×10$^5$ cells/ml in URA drop out medium was prepared from the yeast strains. 75 μl cell suspension was then added to columns 2 through 12 giving 4.5 ×10$^4$ cells/well. The plates were incubated at 28° C. for 24–48 hr. Growth in the presence and absence of echinocandin was measured by absorbance at 600 nm.

EXAMPLE 7

Glucan synthase assay

Membrane extracts were prepared from mutant and wild-type cells grown to logarithmic phase CKang and Cabib, *PNAS*, 83, 5808–5812, 1986). After homogenization with glass beads, unbroken cells and debris were removed by low speed centrifugation (1,000 ×g for 5 min). The supernatant fluids were centrifuged at 100,000 ×g for 60 min, and the resulting pellets were washed with 2.5 ml (per gram of wet cells) of buffer containing 0.05M potassium phosphate (pH 7.5), 0.5 mM DTT, and 1.0 mM PMSF. The washed pellet was resuspended in the same buffer containing 5% glycerol. This protein extract served as the source for both 1,3-β-glucan synthase and the chitin synthases utilized in the enzymatic assays.

Protein concentrations were determined using BCA protein assay reagent kit (Pierce Corp.), utilizing bovine serum album (BSA; Pierce Corp.) as a standard. The 1,3-β-glucan synthase reactions were performed as previously described (Cabib, E., and M. S. Kang. 1987. Fungal 1,3-b-glucan synthase, *Methods Enzymol.* 138: 637–642). Briefly, an 80 ml reaction contained 125 mM Tris HCL (pH70.5), 0.25 mM dithiothretol, 30 mM KF, 0.3M glycerol, 0.23% BSA, 0.125 mM PMSF, 2 mM UDP-glucose, 10 mM guanosine 5'-(g-thio) triphosphate (GTPγS), 0.1 nmol UDP-[$^3$H]glucose (Amersham; 4.5 Ci/mmol;) plus 25 mg of membrane protein extract. The reactions were performed in the presence of 0.0, 0.1, 0.5, 5, 25 and 50 mM L,733-560 for dose titration of the drug. Following incubation at 25° C. for 150 minutes, the

[³H]-glucose incorporated into trichloroacetic acid-insoluble material was collected onto glass fiber filters (102× 258 mm) and measured using a betaplate liquid scintillation counter (Cambridge Technologies Inc.; series 2800 harvester) at 25% efficiency. The product of such reactions was verified by solubilization by laminarinase (Sigma, #L9259) but not by α-amylase (Sigma, #A2643).

EXAMPLE 8

Chitin synthase assay

A previously described chitin synthase assay was used (Kang, M. S., N. Elango, E. Mania, J. Au-Young, P. W. Robbins, and E. Cabib. 1984. Isolation of chitin synthetase from *Saccharomyces cerevisiae*. Purification of an enzyme by entrapment in the reaction product. *J. Biol. Chem.* 259:14966–14972). Approximately 125 mg of membrane protein extract was trypsin-activated and used to catalyze chitin synthase reactions. A reaction of 100 ml contained 50 mM Tris HCl, pH 7.5, 40 mM MgCl, 32 mM N-acetylglucosamine (GlcNAc), 1 mM UDP-N-acetyl-[¹⁴C]glucosamine ($4\times10^5$ cpm/umol), 0.8 mg/ml digitonin. The reactions were performed in the presence of 0.0, 0.125, 0.5, 2 and 8 μM of nikkomycin Z. After 30 minutes of incubation at 30° C., the reaction products were precipitated with 10% trichloroacetic acid and collected onto Whatman glass microfiber GF/A discs followed by counting of the incorporated [¹⁴C]-GlcNAc.

EXAMPLE 9

Isolation of Spontaneous Echinocandin-Resistant Mutants

To isolate mutants in genes involved in biosynthesis of 1,3-β-glucan, pneumocandin B compound, L-733,560 was used to identify resistant mutants in strain X2180-1A. Approximately 40 spontaneous mutants capable of colony formation in the presence of 7.5 mM of L-733,560 were isolated as follows: wild-type strain X2180-1A was grown to stationary phase in SD minimal medium. Approximately 1–3 $\times10^6$ cells were spread on SD plates containing 7.5, 15 or 45 mM L-733,560. Following incubation at 28° C. for four days, echinocandin-resistant colonies appeared at a frequency of $1-3\times10^{-6}$. Mutant strains MS1, MS41 and MS14 were isolated by this procedure. MS14 contains a mutation (fks1-4) in the FKS1 gene. MS1 and MS41 contain gls1-1 and gls1-2 mutations, respectively.

EXAMPLE 10

EMS Mutagenesis and Isolation of Strain MS43 Carrying the gls1-3 mutation

YPAD broth (5 ml) was inoculated with an overnight culture of strain X2180-1A to give initial cell density of 1×10⁶ cell per ml and incubated at 30° C. overnight. A 2.5 ml aliquot of the overnight culture was washed twice in 50 mM KPO₄ buffer, pH 7.0 by centrifugation, and resuspended in 10 ml of the same buffer. To a 5 ml aliquot of the washed cells, 150 μl of ethyl methanesulfonate (EMS) was added. The suspension of treated cells was vonexed and incubated at 30° C. for 1 hr. The other 5 ml of the washed culture was kept on ice untreated. To the 5 ml treated cells, an equal volume of a freshly prepared 10% (w/v) filter-sterilized sodium thiosulfate solution was added and mixed. Cells were collected, washed twice with sterile water, resuspended in 5 ml YPAD, and incubated at 24° C. for 4–6 hr. Appropriate cell dilutions were plated on minimal medium (SD). The untreated culture was diluted and plated by the same way. After 3 days of growth at 24° C., colonies were replica-plated onto YPAD medium with and without 0.001 μg/ml L-733,560 and incubated at 30° C. Of 1000 colonies tested by this procedure, 10 colonies were resistant to L-733,560. One of these resistant strains, designated MS43, was shown to contain the gls1-3 mutation as described below.

EXAMPLE 11

Genetic Analysis

Outcrosses were performed between each of three mutant strains (MS1, MS41, MS43) and the wild-type strain GG100-14D. Tetrad analysis revealed that L-733,560-resistance segregated as a single trait in all three mutant strains (FIG. 1). Single gene mutations are expected to segregate in a mendelian fashion (2:2) upon crossing of a mutant to a wild-type strain.

The mutations in the three mutant strains were tested for dominance or recessiveness by mating the MATa echinocandin-resistant mutants to the MATa echinocandin-sensitive strain GG100-14D (wild-type). All three resulting MATa/MATa heterozygous diploid strains, D2 (MS1×GG100-14D), D12 (MS41×GG100-14D and D28 (MS43× GG100-14D), exhibited sensitivity to L-733,560, indicating that strains MS1, MS41 and MS43 contain recessive mutations.

The recessive nature of these mutations was verified by the finding that the heterozygous diploids D2, D12 and D28 exhibited the wild-type rather than the mutant phenotype. Complementation tests were performed using drug-resistant segregants from the D2, D12 and D28 diploids. The diploids formed between resistant isolates carrying mutations from MS1, MS41 or MS43 (D132, D136, D137, D140, D141 and D142) exhibited resistance to L-733,560, indicating lack of complementation among the three mutations.

These results indicate that the three independently isolated mutations gls1-1 (strain MS1), gls1-2 (strain MS41) and gls1-3 (MS43) comprise one complementation group. Mutations in different or unlinked genes can complement a specific phenotype. Mutations in the same gene or in tightly-linked genes usually fail to complement each other and are, therefore, classified as one complementation group.

EXAMPLE 12

Genetic Mapping of the glsl Mutations

Genetic analysis of the meiotic segregants of 37 tetrads resulting from outcrossing MS41 to GG100-14D lead to mapping of the gls1-1 mutation to within 1.35 centi Morgan from the MAT locus on chromosome III (Table 2). Similar analysis revealed that both gls1-2 (strain MS41) and and gls1-3 (strain MS43) are linked to the MAT locus. The parental ditype class of tetrads (PD) was the only class obtained from crosses between GG100-14D and MS1 (12 tetrads) or between GGI00-14-D and MES43 (19 tetrads). If the mutations were in unlinked loci or in genes located on different chromosomes, then a predominant tetratype class (T) of progeny would have been expected. The phenotypes of the mutant and the wild-type strain used in the genetic crosses are given below:

| Strain | Phenotype |
| --- | --- |
| MS1 | Mat a, Echinocandin$^R$ |
| MS41 | Mat a, Echinocandin$^R$ |
| MS43 | Mat a, Echinocandin$^R$ |
| GG100-14D | Mat a Echinocandin$^S$ |

The tetrads resulting from outcrossing a MATa resistant mutant (strains MS1, MS41 or MS43) to a MATa sensitive wild-type (GG100-14D) should exhibit one of the three tetrad types as follows:
1. Parental ditype phenotypes (PD): Mat a Echinnocandin$^R$ Mat a Echinocandin$^S$
The siblings exhibit the phenotypes of either parent.
2. Non-parental ditype phenotypes (NPD): Mat a Echinocandin$^S$ Mat a Echinocandin$^R$
The siblings exhibit phenotypes of neither parent.
3. Tetratype phenotypes (T): The siblings exhibit both parental and non-parental ditype phenotypes (Mat a Echinocandin$^S$, Mat a Echinocandin$^R$, Mat a Echinocandin$^R$, Mat a Echinocandin$^S$.

The data obtained from outcrossing the three gls1 mutants to the wild-type strain GG 100-14D is summarized in Table 2.

TABLE 2

GENETIC MAPPING OF THE GLS1 MUTATIONS

| Interval | Ascus Type | | | Map Distance (cM) |
| --- | --- | --- | --- | --- |
| | PD | NPD | T | |
| gls1-1 - MAT | 36 | 0 | 1 | 1.35 |
| gls1-2 - MAT | 12 | 0 | 0 | |
| gls1-3 - MAT | 19 | 0 | 0 | |

A NPD ratio of <1 indicates linkage. This data indicates that the three gls1 mutations are linked to MAT. The map distance between two loci is calculated as follows: 100 (½T)+NPD/Total number of tetrads The distance between gls1-1 and MAT=50/37=1.35 centi Morgan.

EXAMPLE 13

Characterization Of Strain MS1 Mutant

Strain MS1 exhibits a bilateral mating defect, (i.e., mating for the production of homozygous diploids containing two copies of gls1-1 is very ineffecient). The resultant homozygous diploids do not form spores upon subculturing on sporulation media. The homozygous diploids are osmotically unstable and burst when suspended in water.

In contrast, mating between wild-type cells and cells containing any of the three gls1 mutations for production of heterozygous diploids is normal.

Figure 3B:
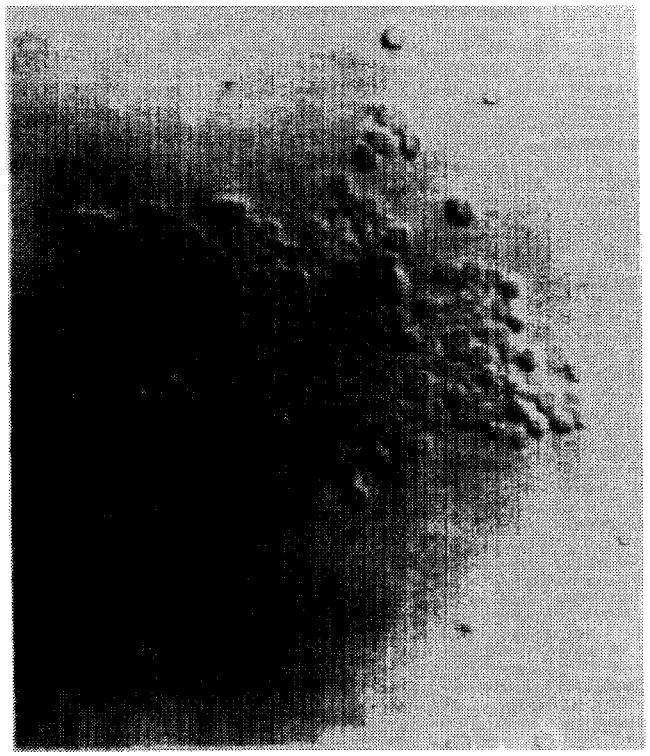
FIG. 3. Morphological defects in strain MS1 (gls1-1 mutant) showing aggregates of cells (A) that start to lyse towards the center of the aggregate (B) before all the cells in the aggregate lyse (C&D).
Figure 3A:
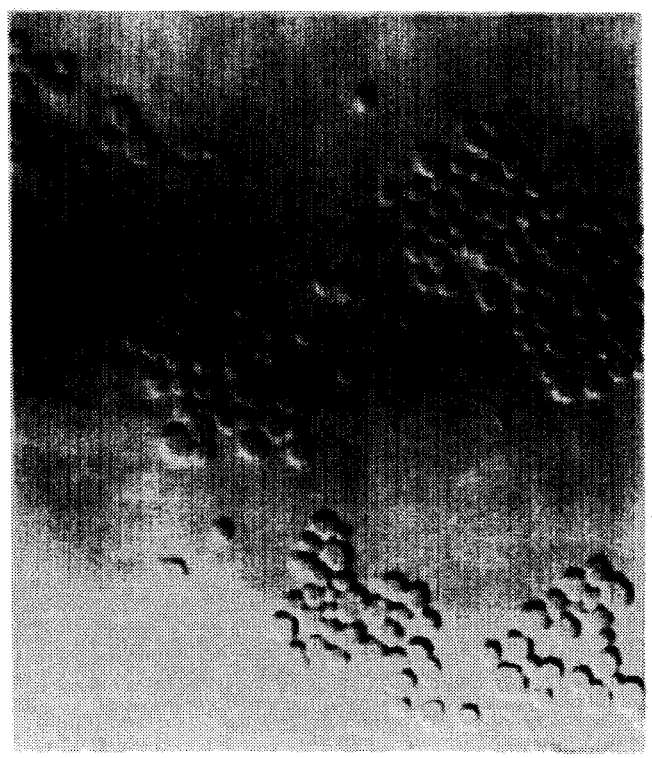

Morphologically, MS1 cells show some aggregated cells (FIG. 3), multiple buds, and occasional flocculated growth in YPAD medium at 30° C. Strain MS1 also grows slower in YPAD than its wild-type parental strain. This slow growth is characterized by a long lag period before the cells enter the division cycle.

EXAMPLE 14

Effect of Antifungal Drugs on Strain MS1

Strain MS1 did not exhibit multiple drug resistance when tested against a panel of more than 30 inhibitors affecting cell wall, membrane, sterol, and protein synthesis.

Figure 2:
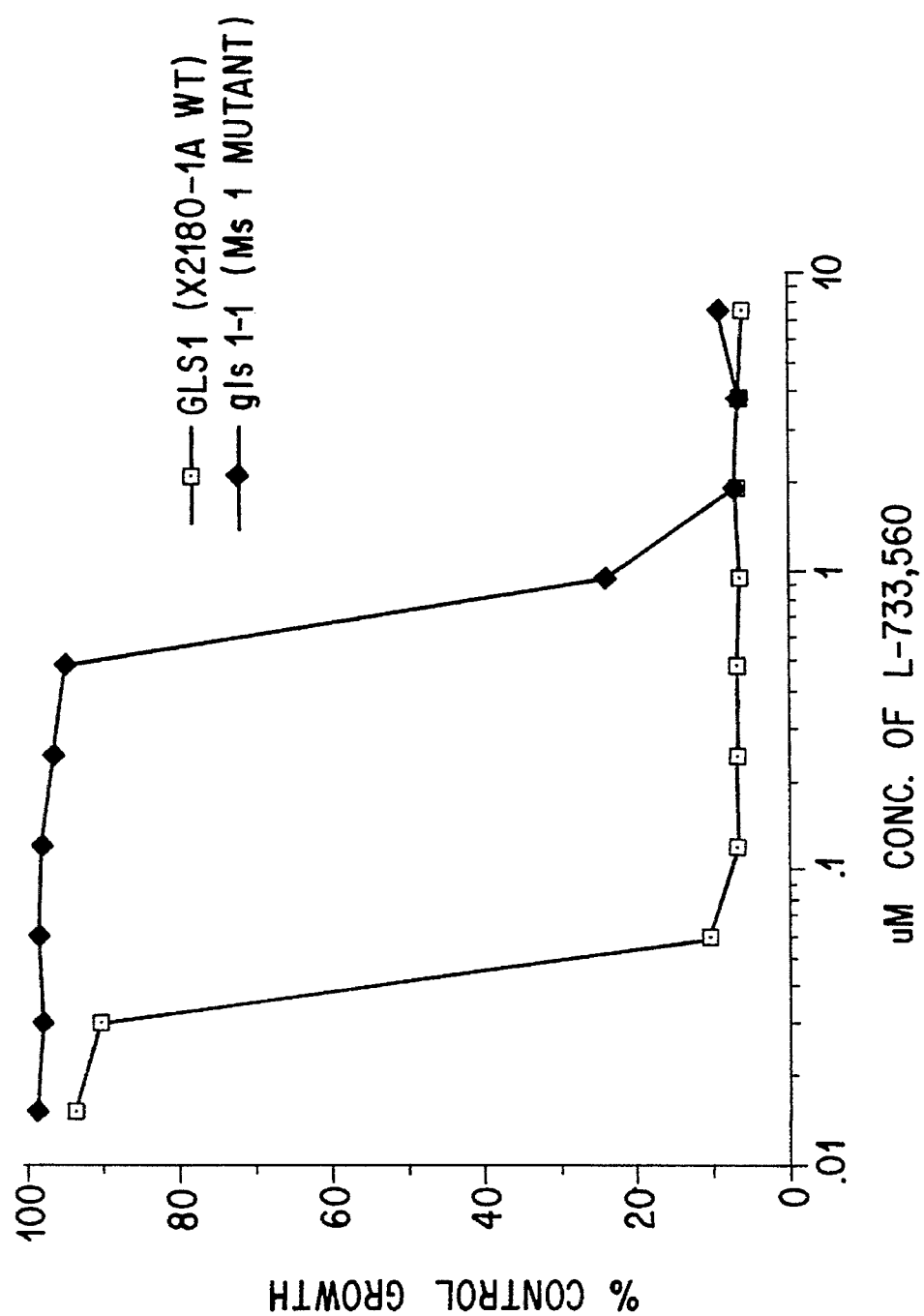
FIG. 2. Strain MS1 (gls1-1 mutant) was tested for resistance to the echinocandin L-733,560 by the broth microdilution assay.
Figure 10A:
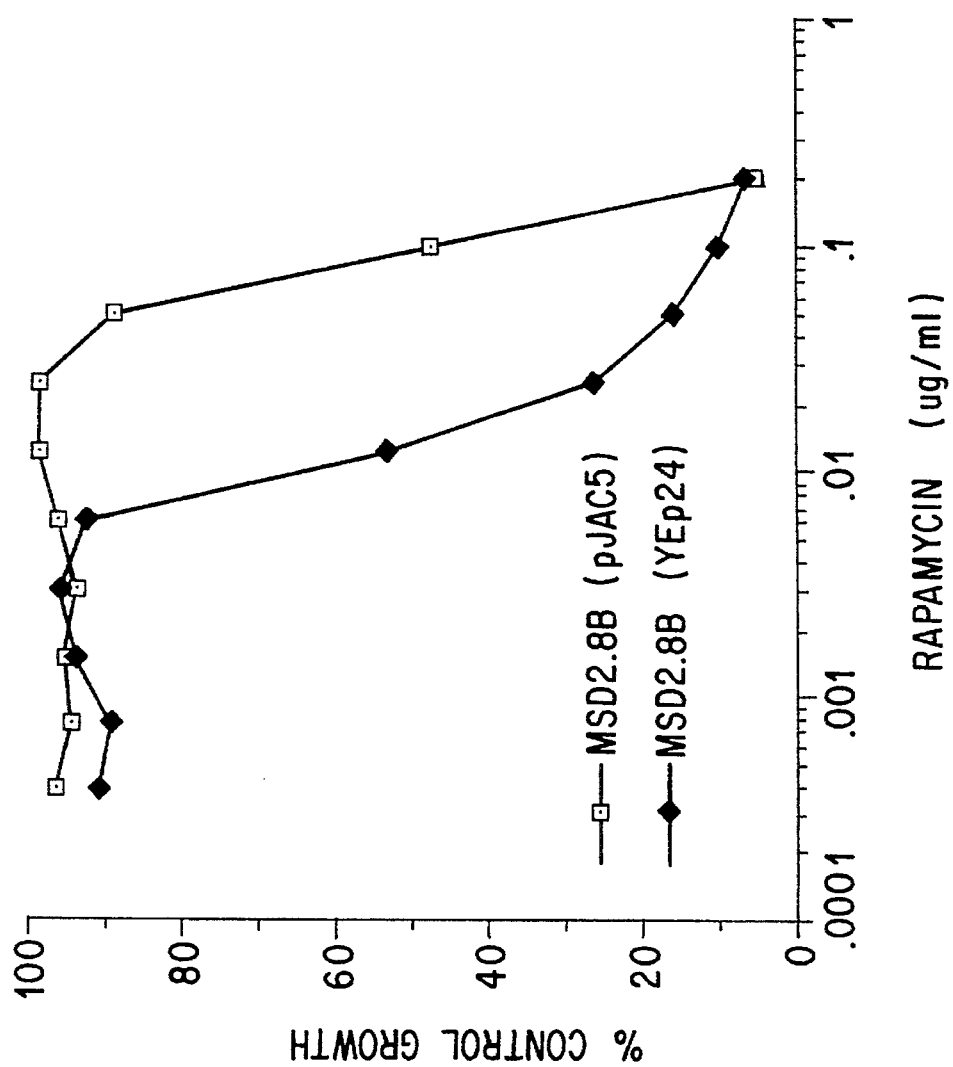
FIG. 10. GLSI complements the papulacandin- and the rapamycin-supersensitivity phenotypes of the gls1-1 mutation. (A) Effect of rapamycin on cells carrying the gls1-1 mutation. (B) Effect of papulacandin B on the same mutant cells. The mutant cells transformed with GLS1 on a plasmid reverse sensitivity to both drugs.
Figure 10B:
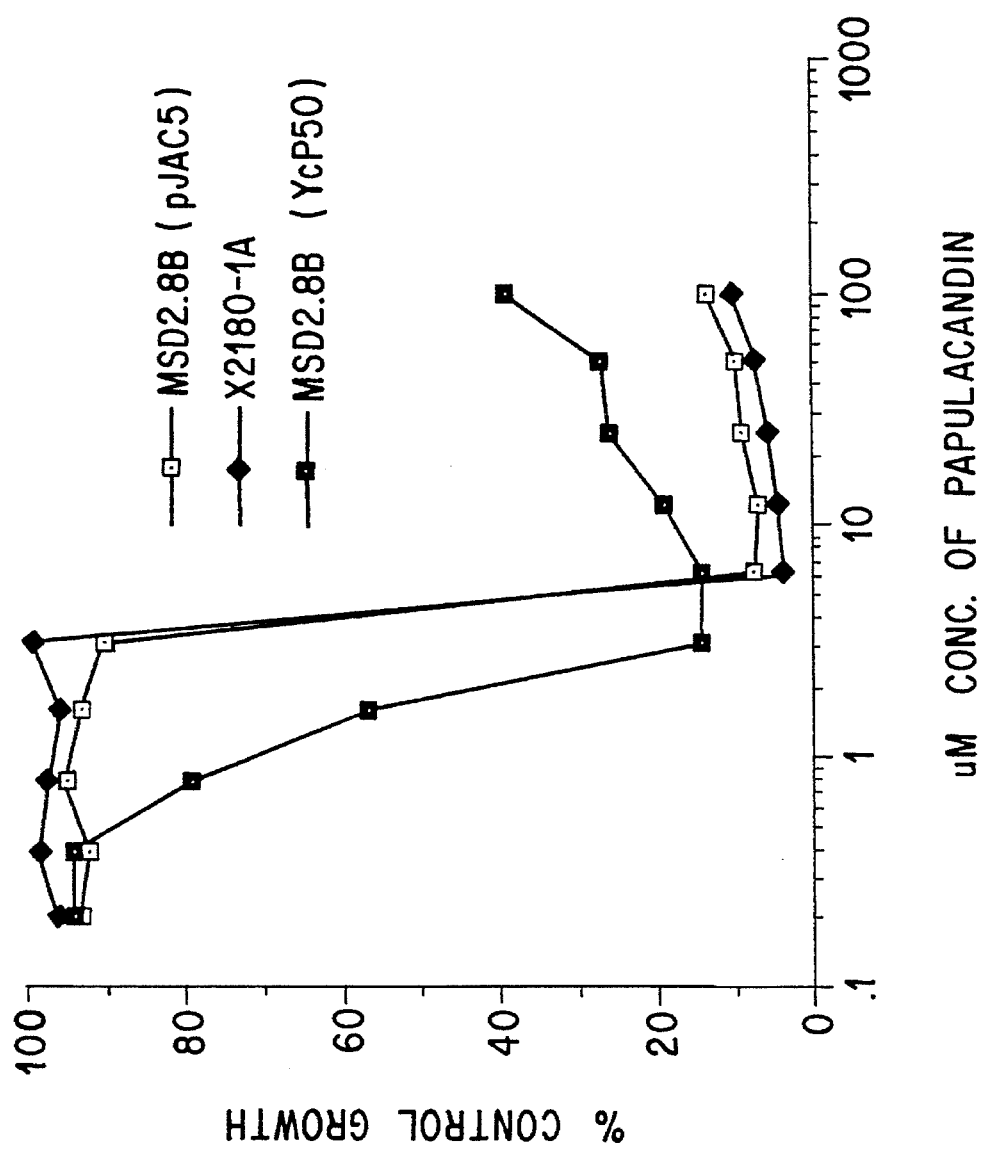

In addition to its resistance to L-733,560 (FIG. 2), MS1 cells are more sensitive to the 1,3-β-glucan synthase inhibitor, papulacandin, and to the immunosupressant rapamycin, than is the wild-type parental strain (FIG. 10).

EXAMPLE 15

Levels of 1,3-β-Glucan Synthase and Chitin Synthase Activities

Figure 4A:
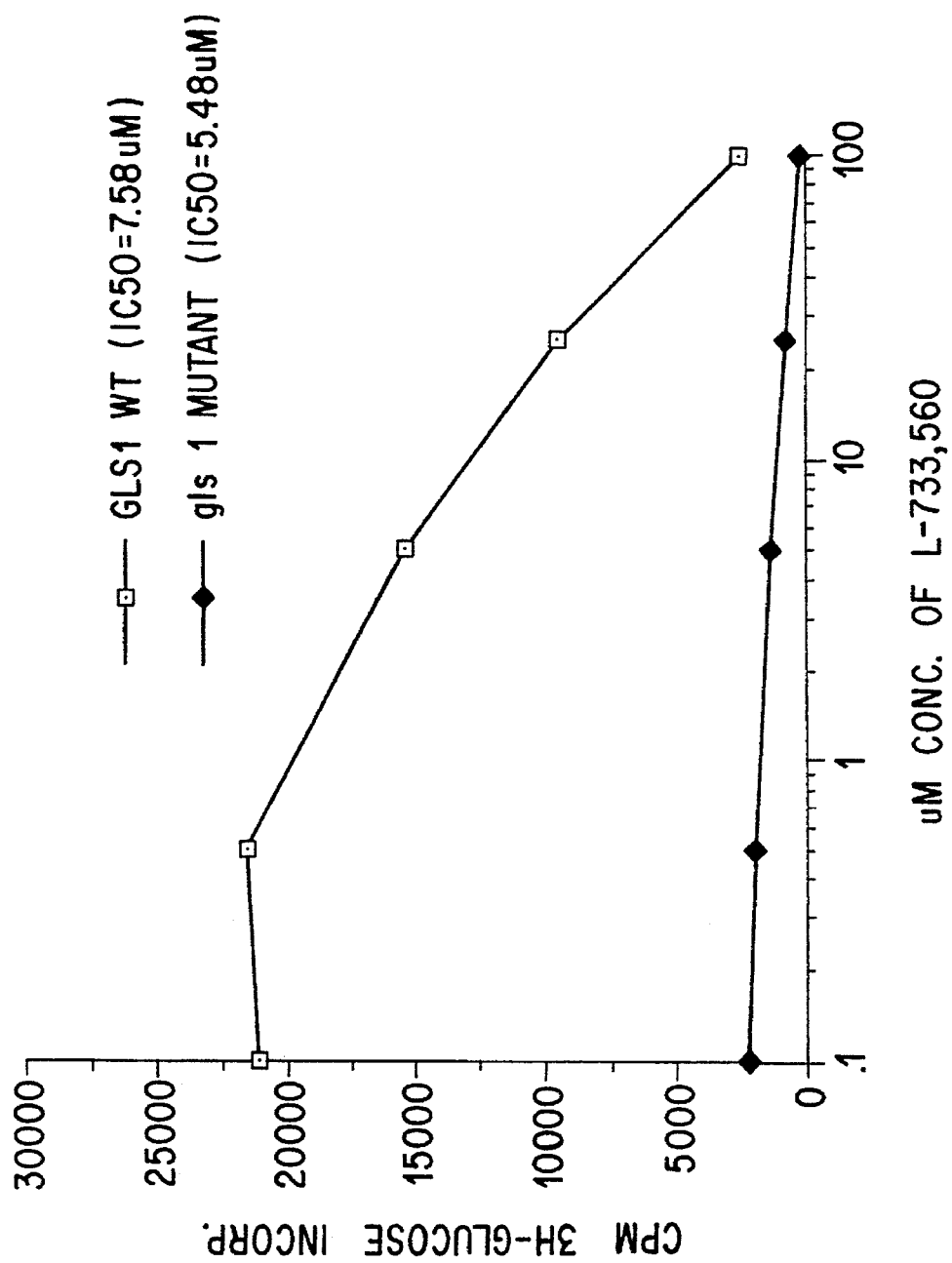
FIG. 4. Effect of L-733,560 and Nikkomycin Z on 1,3-β-D glucan synthesis and chitin synthesis. Membrane extracts prepared from X2180-1A (wild-type) and from MS1 (gls1-1 mutant) were used to catalyze 1,3-β-glucan synthase reactions (A) and chitin synthase reactions (B). UDP-glucose (A) and N-acetylglucosamine (B) were used as substrates.
Figure 4B:
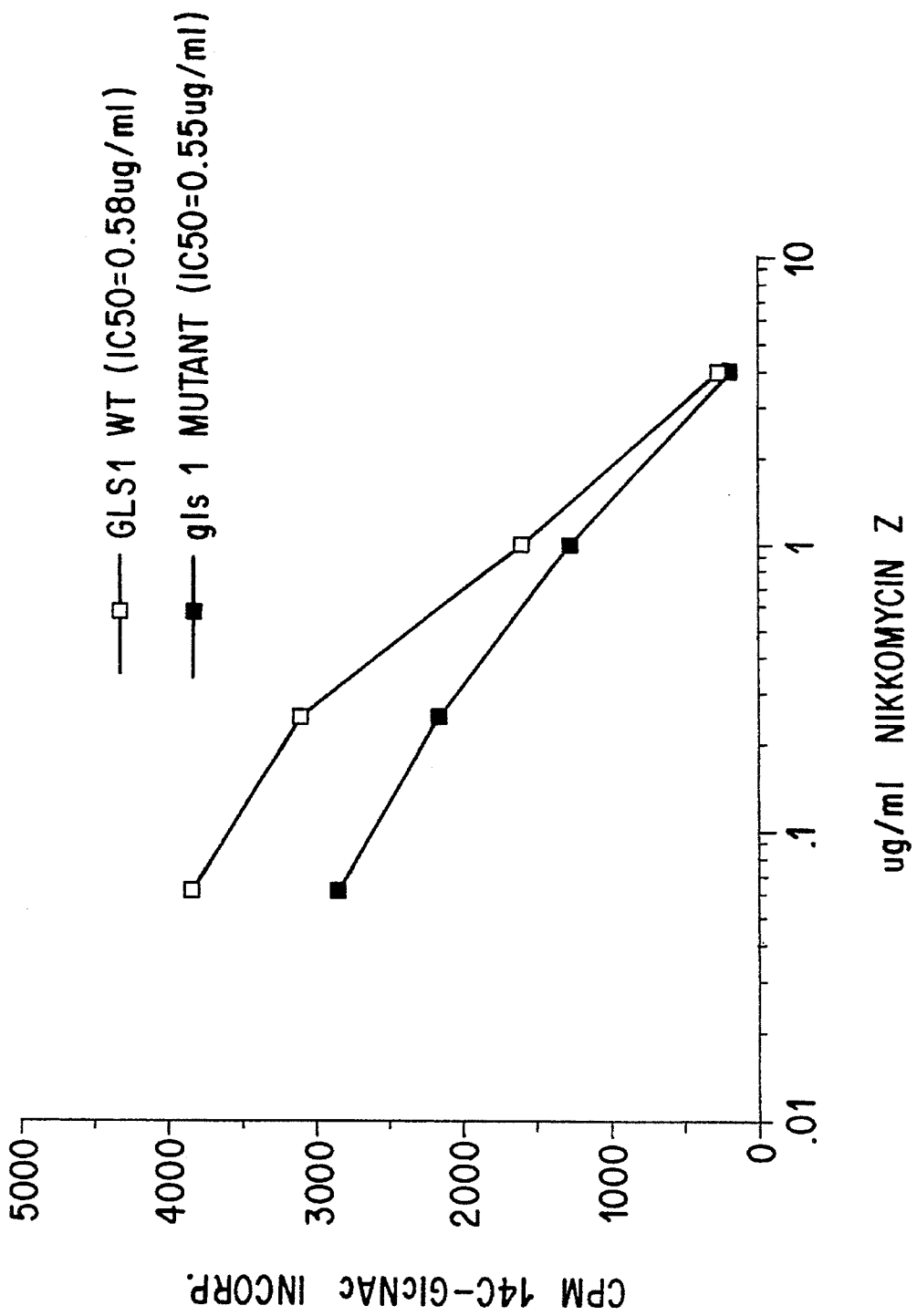

Crude enzyme preparations from cell membranes were tested for 1,3-βglucan synthase and chitin synthase activities. The sensitivity of in vitro synthesis of those polymers to L-733,560 and Nikkomycin Z was determined (FIG. 4).

These experiments showed that glucan synthesis activity of MS1 is reduced (80% less activity) relative to wild-type cells.

EXAMPLE 16

Stimulation of 1,3-β-D-Glucan Synthesis by GTPγS

To study activation of 1,3-β-glucan synthesis by GTPγS incorporation of UDP-glucose into 1,3-β-D glucans, in absence and in presence of 3.3 uM GTPγS was measured. The glucan synthesis of the MS1 mutant enzymatic activities was stimulated (approximately 19-fold) by GTPγS. This contrasts the 6-fold stimulation by the MS1 mutant enzyme (FIG. 4).

Figure 5:
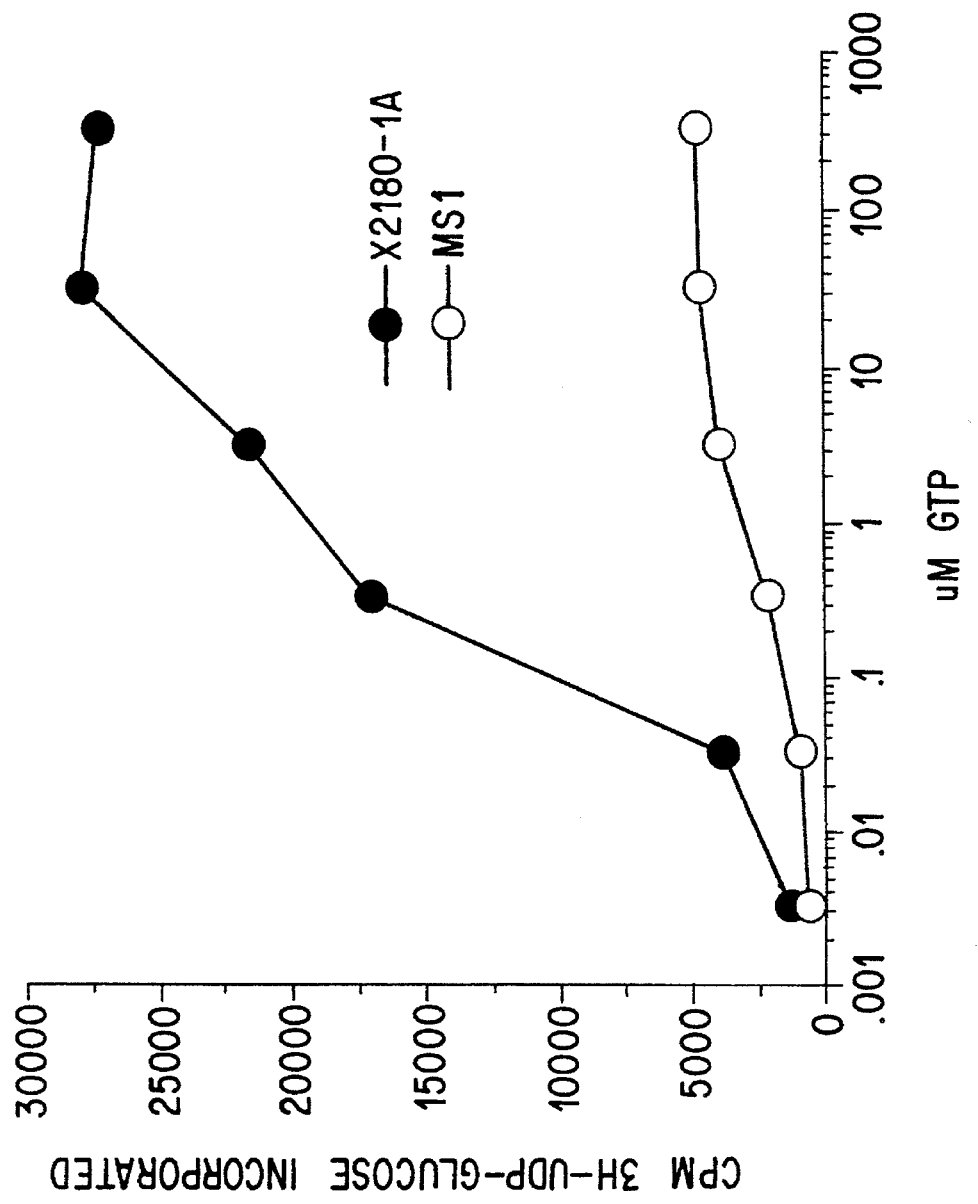
FIG. 5. Effect of GTPγS on 1,3-β-glucan synthase activity. Membrane extracts from wild-type and mutant strains were used to prime 1,3-β-glucan synthase reactions in the presence of increasing concentrations of GTPγS.

In another experiment the stimulation of the mutant and the wild-type membranes by different concentrations of GTPγS was studied. The MS1 mutant enzymatic activity responded rather poorly to increasing concentrations of GTPγS (FIG. 5).

EXAMPLE 17

Isolation of the GLS1 Gene by Functional Complementation and by Hybridization

The GLS1 gene was cloned by complementation of the echinocandin-resistance phenotype. Yeast strain D2.8B (MAT a, ura3-52, gls1-1) was transformed with a yeast genomic DNA library in the centromeric vector YcP50 (Rose, M.D., et al. 1987. Gene. 60:237–243), followed by selection of transformants on Ura-drop-out medium. Transformants (2400) were picked onto master plates of Ura-drop out medium and replica-plated onto plates containing the same medium supplemented with 0.0 or 7.5 µM of L-733-560. Following incubation at 30° C. for 2–3 days, 4 sensitive colonies colonies were isolated. One of these four colonies, designated D2.5B (pJAC2-1) was shown to contain a complementing plasmid, pJAC2-1. In a separate experiment, a 1.5 kb DNA fragment representing a sequence located at about 7 kb to the left of MAT was amplified by PCR, radiolabeled and used as a probe to screen a YCp50-based yeast genomic library by colony hybridization (Sambrook, J., et al., supra). Screening of approximately 4800 bacterial colonies by this procedure resulted in a hybridizing clone containing a plasmid designated pJAC2-2.

pJAC2-1 and pJAC 2-2 contain DNA fragments that have identical restriction maps. pJAC2-2 was introduced into strain D2.8B. Three yeast transformants were tested and shown to have acquired a wild-type level of sensitivity to L-733-560. Furthermore, membrane extracts prepared from the transformants reversed the low level of 1,3-β-glucan synthase specific activity associated with the membranes of the untransformed mutant.

A yeast transformant designated D2.8B (pJAC2-2) was cured of its transforming plasmid, pJAC2-2, by three successive rounds of overnight growth in YPAD broth followed by plating on YPAD plates for single colony formation. Cured clones lost the plasmid and exhibited resistance to L-733,560.

EXAMPLE 18

Determination of the Gls1-1 Minimum Complementing Fragment

The gls1-1 complementing region of pJAC2 was defined by digesting with restriction enzymes that cut within the cloned insert DNA (FIG. 6). Plasmids containing restriction fragments subcloned in YcP50 were propagated in E. coli DH5a, characterized with regard to restriction patterns and then introduced into mutant yeast strain MSD2.8B. The resulting yeast transformants were tested for growth rate and drug-resistance phenotype. The gls1-1 complementing activity was present in approximately 4 kb Kpnl fragment (FIG. 1). Further complementation analysis defined a 1.6 kbp DpnI fragment containing the GLS1 gene.

Using restriction analysis and subcloning of smaller DNA fragments from the original 17 kb library clone, a 4 kb Kpnl fragment of pJAC2 was cloned in the single copy vector YCpLac33 to yield pJAC1. pJAC1 complemented the MS1 mutant phenotypes.

Figure 7:
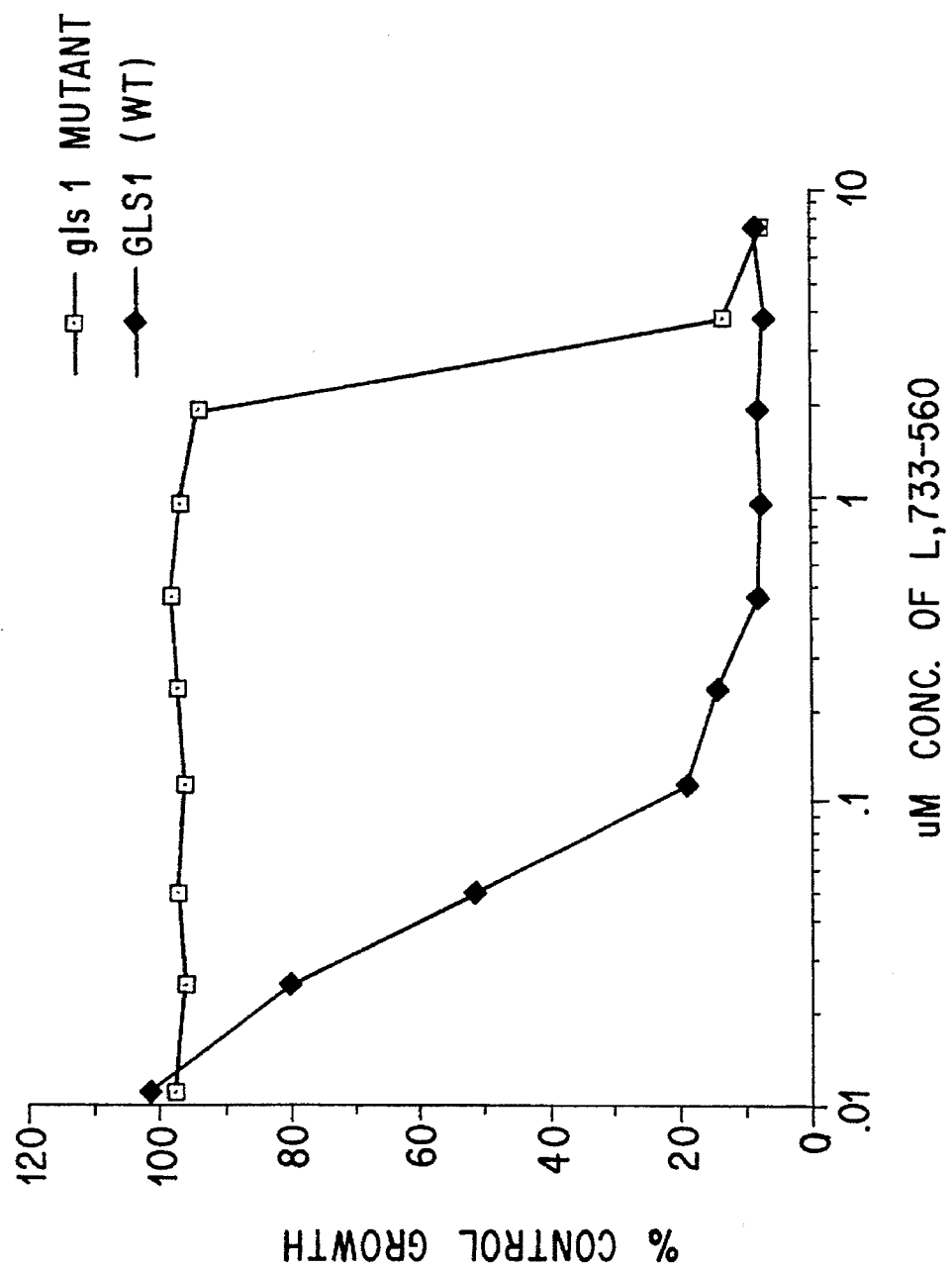
FIG. 7. GLS1 mediates sensitivity to echinocandins.
Figure 8:
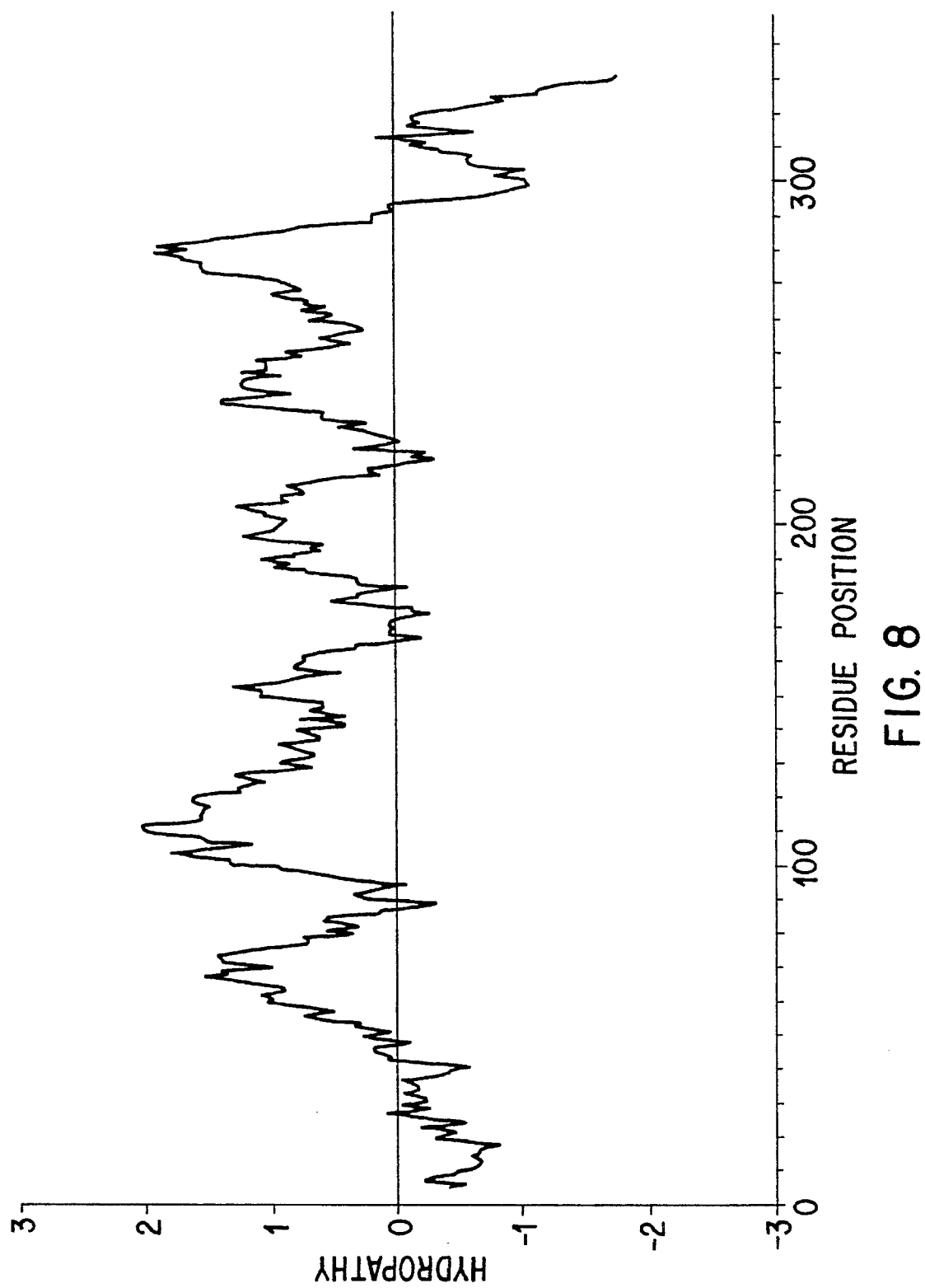
FIG. 8. Hydropathy plot of the 348 amino acid GLS1 gene product.

By similar analysis a 1.6 kb DpnI fragment from pJAC2 was cloned into the HincII site of the bacterial vector pUC18 to produce a plasmid designated pJAC4. A BamH1/Sph1 1.6 kb fragment containing GLS1 was purified from pJAC4 and subcloned into both YEp24 and YCp50 plasmids (digested with BamH1 and SPH1) to yield pJAC5 and pJAC3 respectively. Both plasmids (pJAC3 and pJAC5) complemented the gls1-1 drug-resistance/sensitivity phenotypes (FIGS. 7,8).

EXAMPLE 19

Nucleotide and Deduced Amino Acid Sequence Analysis of GLS1

The dideoxy chain termination method was used to determine the nucleotide sequence of the 5' end of GLS1. The sequence was determined for the first 200 bp and compared with the open reading frame (ORF) YCR34 on Chromosome III (Olwer, S. et al., 1992, *Nature* 357:38–46). The sequences were identical over the 200 bp compared. These results suggested the identity of GLS1 and the YCR34 ORF. The nucleotide and the predicted amino acid sequences of GLS1/YCR34 are shown in FIG. 9.

The 600 bp of sequence in the 5' untranslated region of GLS1/YCR34 contains four candidate promoter 'TATA' boxes. In addition, there are two candidate UAS elements with a strong homology to the yeast HAP1 binding site. Thus, the promoter region of GLS1 shows a striking similarity to that of the yeast gene CYC1. The sequence matches of the 4 'TATA' elements are almost identical in the two genes. The UAS sequences also show a strong homology to the UAS1 of CYC1. This suggests that GLS1 expression may be controlled in a fashion similar to that of CYC1.

The 348 amino acid putative protein product of GLS1/YCR534 was compared to protein databases. No significant homology with known proteins was found. A hydropathy analysis was performed on the 348-residue amino acid sequence, using the Kyte and Doolittle algorithm (FIG. 10). The putative protein product is basic (pI=10.3) and hydrophobic. There are several leucine zipper motifs in the sequence, indicating that the protein product may fold as a dimer.

EXAMPLE 20

GLS1 Gene Disruption

A chromosomal deletion of the GLS1 gene was generated by one-step gene disruption (Rothstein, R. J., 1983, *Methods Enzymol.* 1012:202–211) to test whether GLS1 is essential. A 1.2 kb region of plasmid pJAC4, containing most of the GLS1 coding sequence, was deleted as a NruI-EcoRV fragment. The deleted region of pJAC4 was replaced by blunt-end ligation with a 1.5 kb DNA fragment containing URA3 gene. The disrupted copy of GLS1 was excised as a 2.7-kbp HindII/XbaI fragment, and used to transform the two GLS1-containing wild-type strains GG100-14D and D2.5A.

The resulting Ura$^+$ yeast transformants were tested for echinocandin-resistance. Two transformants (GGDglsl and D2.5ADglsl) acquired resistance to L-733,560 and were analyzed further (FIG. 9). The alteration of the GLS1 locus was confirmed by Southern hybridization analysis. The viability of the haploid strains with GLS1 deletions indicate that the gene is not essential for growth.

EXAMPLE 21

GLS1 Homologues Exist in Pathogenic Species

Yeast 1,3-β-D glucan synthase can be fractionated into a soluble and insoluble fractions by treating yeast membrane preparations with salt and detergent. A glucan synthase activity can be reconstituted by mixing the two fractions in presence of GTP. Cabib and coworkers have demonstrated that the solubilized fraction is exchangeable between yeast and other fungi. This suggests a possible homology between glucan synthesis enzymes amongst fungi.

Figure 11:
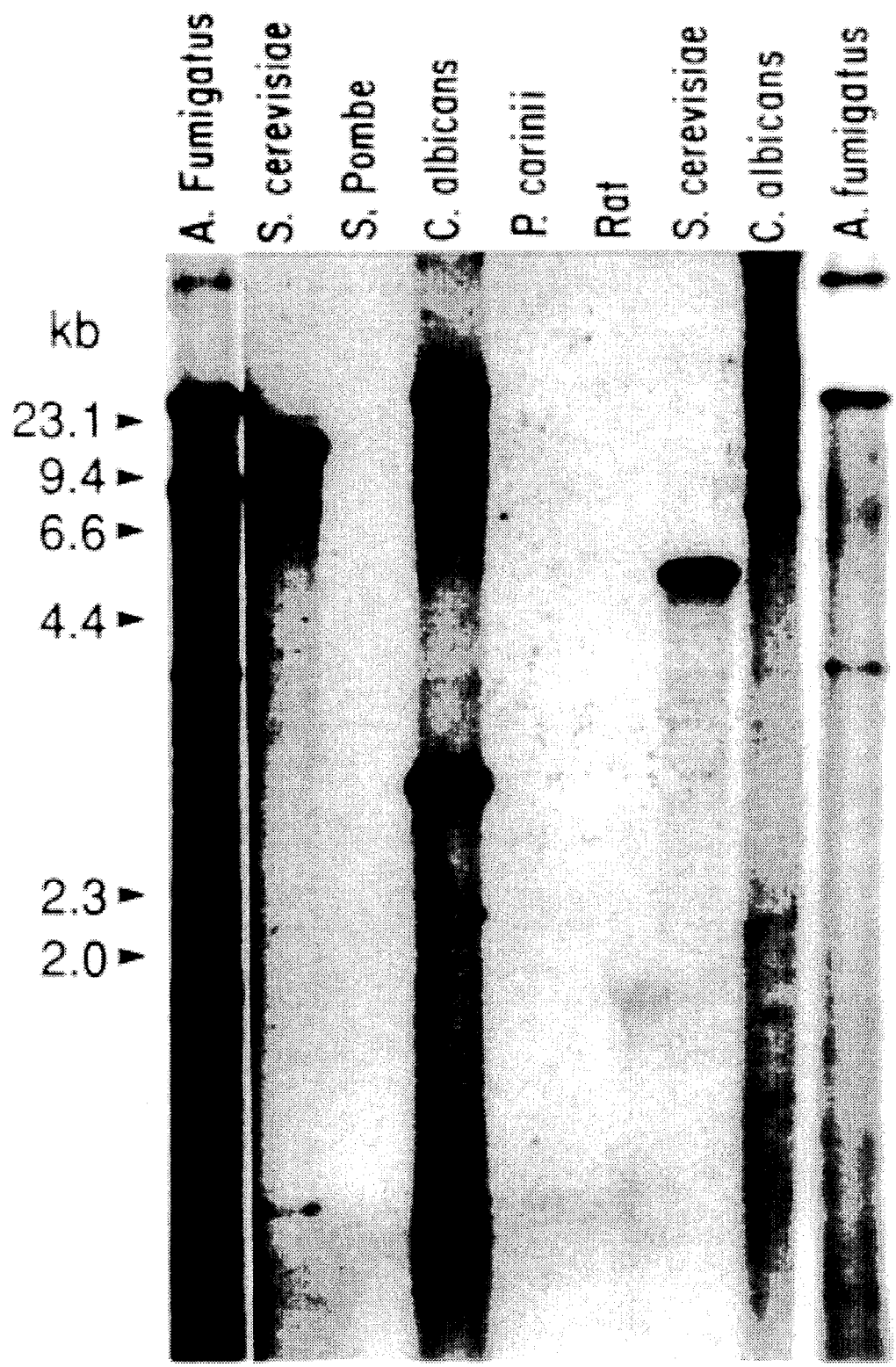
FIG. 11. Southern hybridization of genomic DNA. To test whether homologues of the cloned GLS1 exist in other fungi, DNA probes from the GLS1 gene of *S. cerevisiae* were hybridized to genomic DNA from several heterologous species. The existence of GLS1 homologues in several species, including *Candida albicans, Aspergillus fumigatus, Pneumocysts carinii* and *Schizosaccharomyces pombe* is shown.

To test whether homologues of the cloned GLS1 exist in other fungi, genomic DNA from several heterologous species was prepared and a series of PCR and Southern hybridization analysis were performed. The results showed that GLS1 homologues exists in other fungi, including *Candida albicans, Aspergillus fumigatus, Schizosaccharomyces pombe,* and *Phytophthora infestans* (FIG. 11).

EXAMPLE 22

Isolation of GLS1 Homologues from Pneumocystis Carinii

Whole rat lungs from *P. carinii*-infected male Sprague-Dawley rats are homogenized with a Brinkmann homogenizer, and DNA is isolated as described (P. A. Liberator, et al., 1992. *J. Clin. Micro.* 30(11): 2968–2974). Two to five micrograms of purified DNA are digested with a restriction endonuclease such as EcoRI, and the fragments are separated on an agarose gel. DNA is transferred to a solid support such as nitrocellulose and probed by the method of Southern (Southern, E. M. 1975. *J. Mol, Biol.* 98:503–517) for fragments with homology to GLS1. By washing the blot at a reduced stringency, weakly homologous genes can be identified.

The *P. carinii* GLS1 homologues are cloned by preparing a mini-library from the region of the agarose gel where the hybridizing fragment was visualized on the Southern blot. Following phenol:CHCl$_3$ extraction to remove contaminants, DNA fragments from this area of the gel are ligated into an appropriate plasmid vector and transformed into *E. coli*. The *E. coli* clones bearing the mini-library are spread onto agar plates and probed for inserts homologous to GLS1 by in situ colony lysis. DNA from individual transformants is transferred to nitrocellulose, hybridized to a radiolabeled GLS1 DNA fragment, washed, and exposed to film. Colonies containing an insert with homology to GLS1 are visualized on the film; plasmid DNA is then isolated from positive clones, propagated, and analyzed. DNA sequence analysis by standard methods is used to establish the extent of homology to GLS1, and functional homology may be demonstrated by expression in *S. cerevisiae* disrupted for GLS1.

EXAMPLE 23

Isolation of GLS1 Homologs from Phytopathogenic Fungi

To clone GLS1 homologs from phytopathogenic fungi such as *Phytophthora infestans*, high molecular weight genomic DNA is isolated by the method described by Atkins and Lambowitz (*Mol. Cell. Biol.*, 5; 2272–2278), partially digested by a restriction enzyme, and cloned into the Stratagene Vector Lambda-Dash using a cloning kit obtained from the manufacturer and methods of the an (Maniatis). The libraries are screened using probes from GLS1.

EXAMPLE 24

The GLS1 mutants (strains MS1, MS41 and MES7-43) are echinocandin-resistant and papulacandin-supersensitive, while the fksl-4 mutant (strain MS14) is echinnocandin-resistant (50 fold more resistant than wild-type) and nikkomycin Z-supersensitive (1000 fold more sensitive). The GLS1 and the fksl-4 mutants can be incorporated into an assay to screen and classify antifungal compounds with chitin and glucan synthase inhibitory effects, based on their differential resistance/sensitivity to the echinocandins, papulacandin and Nikkomycin Z. The data from this assay and the sizes of the zones of growth inhibition in millimeter is given in the following table:

| | | Strain | | |
|---|---|---|---|---|
| Inhibitor | μg/Disc | X2180 (WT) | MS1 (gls1-1) | MS14 (fks1-4) |
| L,733-560 (echinocandin) | 20 | 15 | 12 | 8 vh |
| L-688-786 (echinocandin) | 10 | 0 | 7 vh | 0.0 |
| Aculeacin | 50 | 15 | 9 | 0.0 |
| Papulacandin | 50 | 10 | 20 | 10 h |
| Nikkomycin Z | 10 | 0.0 | 0.0 | 30.0 |
| Rapamycin | 12.5 | 0.0 | 13 | 0.0 |

The MS1 and MS14 yeast strains may be used in an assay to screen for glucan and chitin synthesis inhibitors. This assay can also discriminate between different classes of glucan synthesis inhibitors like papulacandins and echinocandins.

A compound that is active against MS14 but inactive against MS1 and the wild-type strain is a "chitin synthase-type" of inhibitor. A compound that is active against MS1 but less active against the wild-type strain and MS14 is a "papulacandin type" of inhibitor. "Echinocandin-type" inhibitors would exhibit less activity on MS1 cells and lesser activity on MS14 cells relative to the wild-type strain.

EXAMPLE 25

Cloning of GLS1 for Expression of the GLS1 Polypeptide In Other Host Cell Systems (a) Cloning of GLS1 cDNA into a bacterial expression vector. Recombinant GLS1 is produced in a bacterium such as *E. coli* following the insertion of the optimal GLS1 cDNA sequence into expression vectors designed to direct the expression of heterologous proteins. These vectors are constructed such that recombinant GLS1 is synthesized alone or as a fusion protein for subsequent manipulation. Expression may be controlled such that recombinant GLS1 is recovered as a soluble protein or within insoluble inclusion bodies. Vectors such as pBR322, pSKF, pUR, pATH, pGEX, pT7-5, pT7-6, pT7-7, pET, plBI (IBI), pSP6/T7-19 (Gibco/BRL), pBluescript II (Stratagene), pTZ18R, pTZ19R (USB), pSE420 (Invitrogen) or the like are suitable for these purposes.

(b) Cloning of GLS1 cDNA into a viral expression vector Recombinant GLS1 is produced in mammalian host cells, such as HeLa S3 cells, after infection with vaccinia virus containing the GLS1 cDNA sequence. To produce GLS1 :vaccinia virus, the GLS1 cDNA is first ligated into a transfer vector, such as pSC11, pTKgptFl s, pMJ601 or other suitable vector, then transferred to vaccinia virus by homologous recombination. After plaque purification and virus amplification, GLS1:vaccinia virus is used to infect mammalian host cells and produce recombinant GLS1 protein.

EXAMPLE 26

Process for the Production of a Glucan Synthase Subunit Peptide

Recombinant GLS1 is produced by (a) transforming a host cell with DNA encoding GLS1 protein to produce a recombinant host cell; (b) culturing the recombinant host cell under conditions which allow the production of glucan synthase subunit peptide; and (c) recovering the recombinant glucan synthase subunit peptide. The recombinant glucan synthase subunit is purified and characterized by standard methods.

EXAMPLE 27

Compounds that modulate glucan synthase subunit activity may be detected by a variety of methods. A method of identifying compounds that affect glucan synthase subunit comprises:

(a) mixing a test compound with a solution containing glucan synthase subunit to form a mixture;

(b) measuring glucan synthase subunit activity in the mixture: and (c) comparing the glucan synthase subunit activity of the mixture to a standard.

Compounds that modulate glucan synthase subunit activity may be formulated into pharmaceutical compositions. Such pharmaceutical compositions may be useful for treating diseases or conditions that are characterized by fungal infection.

EXAMPLE 28

DNA which is structurally related to DNA encoding glucan synthase subunit is detected with a probe. A suitable probe may be derived from DNA having all or a portion of the nucleotide sequence of the figures, RNA encoded by DNA having all or a portion of the nucleotide sequence of figures, degenerate oligonucleotides derived from a portion of the amino acid sequence of figures or an antibody directed against the peptide encoded by GLS1.

EXAMPLE 29

A kit useful for the detection and characterization of DNA or RNA encoding glucan synthase subunit or glucan synthase subunit peptide is prepared by conventional methods. The kit may contain DNA encoding glucan synthase subunit, recombinant glucan synthase subunit peptide, RNA corresponding to the DNA encoding glucan synthase subunit or antibodies to glucan synthase subunit. The kit may be used to characterize test samples, such as forensic samples or epidemiological samples.

What is claimed is:

1. Isolated DNA encoding glucan synthase subunit in yeast which is

2. The isolated DNA of claim 1 having the nucleotide sequence of SEQ ID NO: 7.

3. Isolated RNA encoded by the isolated DNA of claim 1 or its complementary sequence.

4. An expression vector containing the isolated DNA of claim 1.

5. A recombinant host cell containing the expression vector of claim 4.

6. A process for the production of a recombinant glucan synthase subunit peptide, comprising:

(a) transforming a host cell with the isolated DNA of claim 1 to produce a recombinant host cell;

(b) culturing the recombinant host cell under conditions which allow the production of recombinant glucan synthase subunit peptide; and (c) recovering and purifying the glucan synthase subunit peptide.

* * * * *

SEQUENCE LISTING ( 1 ) GENERAL INFORMATION:

(i i i) NUMBER OF SEQUENCES: 2

(2) INFORMATION FOR SEQ ID NO:1:

(i) SEQUENCE CHARACTERISTICS:
      (A) LENGTH: 1854 base pairs
      (B) TYPE: nucleic acid
      (C) STRANDEDNESS: single
      (D) TOPOLOGY: linear (i i) MOLECULE TYPE: cDNA (x i) SEQUENCE DESCRIPTION: SEQ ID NO:1:

| | | | | | |
|---|---|---|---|---|---|
| ATTTCAGCAT | GCTATTTCTC | AAGGCACTCC | TACTTTCCCT | TTACCGGCCC | CTCGCACTAG | 60 |
| TCCAATAAGT | CGTGCGCCTC | CAAAGTTCAA | TTTTTCGAAT | GATCCGTTGG | CAGCTTTGGC | 120 |
| TGCGGTTGCC | TCCGCGCCAG | ATGCAATGAG | CAGTTTTTA | TCTAAAAAGG | AAAATAATAA | 180 |
| TTGAACAAAC | GGCTGAGACG | GGCAATACAT | ATGCTCTACT | TCTTTTCCAT | CCAATGGTTG | 240 |
| GTGAAACTCT | CGAGCATACA | TTACCTTACG | TGTGTTAGTG | TACTATATTA | TATATATATA | 300 |
| TATGTATATA | TATAAAGGGA | GGAGTTTTTA | ATTATAATTG | TAATTTCGTA | TTTTTTCTGC | 360 |
| ATTATACAGT | TTTTTCCGAT | TTTAAACGAC | TTTATTTAAG | TGTCGTGTAA | ATATGTCACA | 420 |
| TTTTATTTTT | GTACGTATTC | ACATGTCCTG | GCGTGCGGCC | ATTGCTGAAA | ATCGCAAAAC | 480 |
| CCACAGAGAA | ATAAACATCG | CGAAAAGTC | AATGAAAAAT | TGGAAATAT | TTTTCATTTC | 540 |
| ACTATTATCC | ACAAGCAATT | TTGTACAAAG | TGAAAAGGTT | GAACTAATTA | TCTTCGTCTA | 600 |
| GAAGCCATGA | ATTCACTCGT | TACTCAATAT | GCTGCTCCGT | TGTTCGAGCG | TTATCCCCAA | 660 |
| CTTCATGACT | ATTTACCAAC | TTTGGAGCGA | CCATTTTTA | ATATTTCGTT | GTGGGAACAT | 720 |
| TTCGATGATG | TCGTCACTCG | TGTAACTAAC | GGTAGATTTG | TTCCAAGCGA | ATTCCAATTC | 780 |
| ATTGCAGGTG | AATTACCATT | AAGCACTTTG | CCCCTGTGC | TATACGCCAT | CACTGCCTAT | 840 |
| TACGTTATTA | TTTTTGGTGG | CAGGTTTTTG | TTAAGTAAGT | CGAAACCATT | TAAATTAAAT | 900 |
| GGCCTTTTCC | AATTGCATAA | TTTGGTTTTA | ACTTCACTTT | CATTGACGCT | TTTATTGCTT | 960 |
| ATGGTTGAAC | AATTAGTGCC | AATTATTGTT | CAGCACGGGT | TATACTTCGC | TATCTGTAAT | 1020 |
| ATTGGTGCTT | GGACTCAACC | GCTCGTTACA | TTATATTACA | TGAATTACAT | TGTCAAGTTT | 1080 |
| ATTGAATTTA | TAGACACCTT | TTTCTTGGTG | CTAAAACATA | AAAAATTGAC | ATTTTTGCAT | 1140 |
| ACTTATCACC | ATGGCGCTAC | TGCCTTATTA | TGTTACACCC | AATTGATGGG | CACCACATCT | 1200 |
| ATTTCTTGGG | TCCCTATTTC | ATTGAACCTT | GGTGTTCACG | TGGTTATGTA | TTGGTACTAT | 1260 |
| TTCTTGGCTG | CCAGAGGCAT | CAGGGTCTGG | TGGAAGGAAT | GGGTTACCAG | ATTTCAAATT | 1320 |
| ATCCAATTTG | TTTTGGATAT | CGGTTTCATA | TATTTTGCTG | TCTACCAAAA | AGCAGTTCAC | 1380 |
| TTGTATTTCC | CAATTTTGCC | ACATTGTGGT | GACTGTGTGG | GTTCAACAAC | TGCCACCTTT | 1440 |
| GCAGGTTGTG | CCATTATTTC | TTCATATTTG | GTACTATTTA | TTTCATTTTA | CATTAACGTT | 1500 |
| TATAAACGTA | AAGGCACCAA | AACCAGTAGA | GTGGTAAAGC | GTGCCCACGG | CGGTGTTGCC | 1560 |
| GCAAAGGTTA | ATGAGTATGT | TAACGTTGAC | TTGAAAAACG | TTCCTACTCC | ATCTCCATCA | 1620 |
| CCAAAACCTC | AACACAGAAG | AAAAAGGTAA | GTGTAAAATC | TTTGAAGAA | TTTAAGTATT | 1680 |
| CAACTTTCGT | ATATTCGTTT | TTTCTTAGTG | GATCTATTGT | TACTATTATC | ACTATTATTA | 1740 |
| TATTGTAAAA | GACCGGATGG | TTTTGTTATA | TATTACATAC | ACATGTTATC | GTTGAAAAAA | 1800 |
| GTTTTCCGTT | TCCTTTCGAC | AGTCATCAGA | TAATTTTATC | CGAGTCTTTT | ATAT | 1854 |

(2) INFORMATION FOR SEQ ID NO:2:

( i ) SEQUENCE CHARACTERISTICS:
   ( A ) LENGTH: 347 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:2:

```
Met Asn Ser Leu Val Thr Gln Tyr Ala Ala Pro Leu Phe Glu Arg Tyr
 1               5                  10                  15

Pro Gln Leu His Asp Tyr Leu Pro Thr Leu Glu Arg Pro Phe Phe Asn
                20                  25                  30

Ile Ser Leu Trp Glu His Phe Asp Asp Val Val Thr Arg Val Thr Asn
            35                  40                  45

Gly Arg Phe Val Pro Ser Glu Phe Gln Phe Ile Ala Gly Glu Leu Pro
        50                  55                  60

Leu Ser Thr Leu Pro Pro Val Leu Tyr Ala Ile Thr Ala Tyr Tyr Val
 65                  70                  75                  80

Ile Ile Phe Gly Gly Arg Phe Leu Leu Ser Lys Ser Lys Pro Phe Lys
                85                  90                  95

Leu Asn Gly Leu Phe Gln Leu His Asn Leu Val Leu Thr Ser Leu Ser
                100                 105                 110

Leu Thr Leu Leu Leu Leu Met Val Glu Gln Leu Val Pro Ile Ile Val
            115                 120                 125

Gln His Gly Leu Tyr Phe Ala Ile Cys Asn Ile Gly Ala Trp Thr Gln
        130                 135                 140

Pro Leu Val Thr Leu Tyr Tyr Met Asn Tyr Ile Val Lys Phe Ile Glu
145                 150                 155                 160

Phe Ile Asp Thr Phe Phe Leu Val Leu Lys His Lys Lys Leu Thr Phe
                165                 170                 175

Leu His Thr Tyr His His Gly Ala Thr Ala Leu Leu Cys Tyr Thr Gln
            180                 185                 190

Leu Met Gly Thr Thr Ser Ile Ser Trp Val Pro Ile Ser Leu Asn Leu
        195                 200                 205

Gly Val His Val Val Met Tyr Trp Tyr Tyr Phe Leu Ala Ala Arg Gly
    210                 215                 220

Ile Arg Val Trp Trp Lys Glu Trp Val Thr Arg Phe Gln Ile Ile Gln
225                 230                 235                 240

Phe Val Leu Asp Ile Gly Phe Ile Tyr Phe Ala Val Tyr Gln Lys Ala
                245                 250                 255

Val His Leu Tyr Phe Pro Ile Leu Pro His Cys Gly Asp Cys Val Gly
            260                 265                 270

Ser Thr Thr Ala Thr Phe Ala Gly Cys Ala Ile Ile Ser Ser Tyr Leu
        275                 280                 285

Val Leu Phe Ile Ser Phe Tyr Ile Asn Val Tyr Lys Arg Lys Gly Thr
    290                 295                 300

Lys Thr Ser Arg Val Val Lys Arg Ala His Gly Gly Val Ala Ala Lys
305                 310                 315                 320

Val Asn Glu Tyr Val Asn Val Asp Leu Lys Asn Val Pro Thr Pro Ser
                325                 330                 335

Pro Ser Pro Lys Pro Gln His Arg Arg Lys Arg
            340                 345
```